US008652488B2

(12) United States Patent
Orban

(10) Patent No.: US 8,652,488 B2
(45) Date of Patent: Feb. 18, 2014

(54) INSULIN B CHAIN AUTOANTIGEN COMPOSITION

(75) Inventor: Tihamer Orban, Brookline, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 780 days.

(21) Appl. No.: 11/403,580

(22) Filed: Apr. 13, 2006

(65) Prior Publication Data

US 2006/0183670 A1 Aug. 17, 2006

Related U.S. Application Data

(63) Continuation of application No. 10/038,686, filed on Jan. 4, 2002, now abandoned.

(60) Provisional application No. 60/260,068, filed on Jan. 5, 2001.

(51) Int. Cl.
*A61K 39/00* (2006.01)

(52) U.S. Cl.
USPC .................................. 424/198.1; 424/185.1

(58) Field of Classification Search
None
See application file for complete search history.

(56) References Cited

U.S. PATENT DOCUMENTS

| | | | | |
|---|---|---|---|---|
| 4,281,061 A * | 7/1981 | Zuk et al. | ......................... | 435/7.9 |
| 4,317,811 A * | 3/1982 | Bertland et al. | ............ | 424/231.1 |
| 4,795,635 A | 1/1989 | Peleg et al. | | |
| 5,075,110 A * | 12/1991 | Francon et al. | ............ | 424/202.1 |
| 5,447,843 A * | 9/1995 | McGuire et al. | .................... | 435/6 |
| 5,622,649 A | 4/1997 | Hunter et al. | | |
| 5,645,998 A | 7/1997 | Atkinson et al. | | |
| 5,759,551 A * | 6/1998 | Ladd et al. | .................. | 424/198.1 |
| 5,891,435 A | 4/1999 | Muir et al. | | |
| 5,998,366 A | 12/1999 | Tobin et al. | | |
| 6,110,746 A | 8/2000 | Cohen et al. | | |
| 6,462,185 B1 * | 10/2002 | Takakura et al. | ............ | 536/23.1 |
| 7,241,448 B2 * | 7/2007 | Jackson et al. | ............. | 424/213.1 |
| 2003/0045467 A1 | 3/2003 | Orban | | |
| 2005/0186207 A1 | 8/2005 | Bluestone et al. | | |
| 2006/0063256 A1 | 3/2006 | Norment et al. | | |
| 2007/0225210 A1 | 9/2007 | Blackburn | | |

FOREIGN PATENT DOCUMENTS

WO WO2004/110373 12/2004

OTHER PUBLICATIONS

Marketletter, Marketletter Pubs. (UK). Sept. 13, 1999.*
Pozzilli, P., et al. Diabetol. 2000;43:1000-1004.*
Skylar, J., et al. Diabet. Care. 2005;28(5):1068-1076.*
Goodnow, C.C. The Lancet. 2001;357:2115-2121.*
Dong, V.M., et al. Ped. Transplant. 1999;3:181-192.*
Muir, A., et al. J. Clin. Invest. 1995;95:628-634.*
Estuningsih, S.E., et al. Int. J. Parasitol. 1997;27(11):1419-1428.*
Rothel, J.S., et al. Vaccine. 1997;15(5):469-472.*
Aanstoot et al., "Identification and characterization of glima 38, a glycosylated islet cell membrane antigen, which together with GAD65 and IA2 marks the early phases of autoimmune response in type 1 diabetes," J. Clin. Invest., (1996), 97(12):2772-2783.
Alcalde et al., "Cloning of candidate autoantigen carboxypeptidase H from a human islet library: sequence identity with human brain CPH," J. Autoimmun., (1996), 9(4):525-528.
Argentaro, et al., "Linkage analysis of SOX13, the ICA12 autoantigen gene, in families with type 1 diabetes," Molecular Genetics and Metabolism, (2001), 72(4):356-359.
Boitard et al., "Peripherin: an islet antigen that is cross-reactive with nonobese diabetic mouse class II gene products," Proc Natl Acad Sci USA, (1992), 89(1):172-176.
Castano et al., "Identification and cloning of a granule autoantigen (carboxypeptidase-H) associated with type I diabetes," J Clin Endocrinol Metab., (1991), 73(6):1197-1201.
Cox and Coulter, "Adjuvants—a classification and review of their modes of action," Vaccine, (1997), 15(3):248-256.
Dionisi et al., "Target antigens in autoimmune diabetes: pancreatic gangliosides," Ann 1st Super Sanita, (1997), 33(3):433-435.
Dotta et al., "Autoimmunity to the GM2-1 islet ganglioside before and at the onset of type I diabetes," (1996), 45(9):1193-1196.
Elias and Cohen, "Peptide therapy for diabetes in NOD mice," Lancet, (1994), 343(8899):704-706.
Elias et al., "Induction of diabetes in standard mice by immunization with the p277 peptide of a 60-kDa heat shock protein," Eur J Immunol., (1995), 25(10):2851-2857.
Karges et al., "Induction of autoimmune diabetes through insulin (but not GAD65) DNA vaccination in nonobese diabetic and in RIP-B7.1 mice," Diabetes, (2002), 51:3237-3244.
Karlsen et al., "Cloning and primary structure of a human islet isoform of glutamic acid decarboxylase from chromosome 10," Proc Natl Acad Sci USA, (1991), 88(19):8337-8341.
Kasimiotis et al., "Sex-determining region Y-related protein SOX13 is a diabetes autoantigen expressed in pancreatic islets," Diabetes, (2000), 49(4):555-561.
Kukreja et al., "Autoimmunity and diabetes," J. Clinical Endocrin. & Metab., (1999), 84(12):4371-4378.
Leslie et al., "Autoantigens IA-2 and GAD in type I (insulin-dependent) diabetes," Diabetologia, (1999), 42(1):3-14.
Pietropaolo et al., "Islet cell autoantigen 69 kD (ICA69). Molecular cloning and characterization of a novel diabetes-associated autoantigen," J Clin Invest., (1993), 92(1):359-371.
Rabin et al., "Islet cell antigen 512 is a diabetes-specific islet autoantigen related to protein tyrosine phosphatases," J. Immunol., (1994), 152(6):3183-3188.
Ramiya et al., "Immunization therapies in the prevention of diabetes," J. Autoimmun., (1997), 10(3):287-292.

(Continued)

*Primary Examiner* — Gerald R Ewoldt
(74) *Attorney, Agent, or Firm* — Pierce Atwood LLP; Joseph Maraia; Kevin M. Farrell

(57) ABSTRACT

The invention features methods for the prevention or treatment of autoimmune disorders in humans. The methods include administering an autoantigen in combination with an oil-based carrier. Included are methods for the prevention and treatment of diabetes mellitus which include treating a patient with a diabetes type 1 autoantigen, e.g., human insulin B-chain or GAD65, and an oil-based carrier approved for human use. Also included are vaccines and kits for the treatment of diabetes mellitus.

12 Claims, No Drawings

(56) References Cited

OTHER PUBLICATIONS

Ramiya et al., "Antigen based therapies to prevent diabetes in NOD mice," J. Autoimmun., (1996), 9(3):349-356.
Simone et al., "Immunologic "vaccination" for the prevention of autoimmune diabetes (type 1A)," Diabetes Care, (1999), Suppl 2:B7-B15.
Xie et al., "Autoantibodies to IA-2 and IA-2 beta in insulin-dependent diabetes mellitus recognize conformational epitopes: location of the 37- and 40-kDa fragments determined," J Immunol., (1997), 159(7):3662-3667.
Zhang et al., "Autoantibodies to IA-2 in IDDM: location of major antigenic determinants," Diabetes, (1997), 46(1):40-43.
Aruna et al., "Down-regulation of T cell responses to AChR and reversal of EAMG manifestations in mice by a dual altered peptide ligand via induction of CD4+ CD25+ regulatory cells ," J. Neuroimmunol., 177:63-75 (2006).
Bergerot et al., "Insulin B-chain reactive CD4+ regulatory T-cells induced by oral insulin treatment protect from type 1 diabetes by blocking the cytokine secretion and pancreatic infiltration of diabetogenic effector T-cells," Diabetes, 48(9):1720-1729 (1999).
Durinovic-Bello et al., "Predominantly recognized proinsulin T helper cell epitopes in individuals with and without islet cell autoimmunity," J. Autoimmun., 18:55-66 (2002).
Dzhambazov et al., "Therapeutic vaccination of active arthritis with a glycosylated collagen type II peptide in complex with MHC class II molecules," J. Immunol., 176:1525-1533 (2006).
Fineberg et al., "Immunological responses to exogenous insulin," Endocr. Rev., 28:625-652 (2007).
Keller et al., "Insulin prophylaxis in individuals at high risk of type I diabetes," Lancet, 341:927-928 (1993).
Kent et al., "Expanded T cells from pancreatic lymph nodes of type 1 diabetic subjects recognize an insulin epitope," Nature, 435:224-228 (2005).
Mallone et al., "MHC Class II tetramers and the pursuit of antigen-specific T cells: define, deviate, delete," Clin. Immunol , 110:232-242 (2004).
Masteller et al., "Expansion of Functional Endogenous Antigen-Specific CD4+ CD25+ Regulatory T Cells from Nonobese Diabetic Mice," The Journal of Immunology, 175:3053-3059 (2005).
Nakayama et al., "Prime role for an insulin epitope in the development of type 1 diabetes in NOD mice," Nature, 435:220-223 (2005).
Orban et al., "Diabetes Insulin Immune Effect Prevents Diabetes in NOD Mice," Diabetes, 48 (Supp.1):A216-A217 (1999).
Prakken et al. "Heat shock protein 60 and adjuvant arthritis: a model for T cell regulation in human arthritis ," Springer Semin. Immunopathol. 25(1):47-63 (2003).
Quintana et al., "Inhibition of adjuvant arthritis by a DNA vaccine encoding human heat shock protein 60," J. Immunol., 169:3422-3428 (2002).
Seddon et al., "Peripheral Autoantigen Induces Regulatory T Cells that Prevent Autoimmunity," The Journal of Experimental Medicine, 189(5):877-881 (1999).
Shah et al., "A randomized trial of intensive insulin therapy in newly diagnosed insulin-dependent diabetes mellitus," The New England Journal of Medicine, 320:550-554 (1999).
Tang et al., "In Vitro-Expanded Antigen-specific Regulatory T Cells Suppress Autoimmune Diabetes," The Journal of Experimental Medicine, 199(11):1455-1465 (2004).
Tarbell et al., "CD25+ CD4+ T Cells, Expanded with Dendritic Cells Presenting a Single Autoantigenic Peptide, Suppress Autoimmune Diabetes," The Journal of Experimental Medicine, 199(11):1467-1477 (2004).
Tiittanen et al., "Insulin Treatment in Patients with Type 1 Diabetes Induces Upregulation of Regulatory T-cell Markers in Peripheral Blood Mononuclear Cells Stimulated with Insulin In Vitro," Diabetes, 55:3446-3454 (2006).
van Roon et al. "Stimulation of suppressive T cell responses by human but not bacterial 60-kD heat-shock protein in synovial fluid of patients with rheumatoid arthritis," J. Clin. Invest. 100:459-163 (1997).
Lindorfer, "Spectroscopic and Chromatographic Studies of Native and Denatured States of T4 Lysozymes", Current Research in Protein Chemistry, 1990, pp. 309-322 (13 pages).
Nakayama, "Long-Term Prevention of Diabetes and Marked Suppression of Insulin Autoantibodies adn Insulitis in Mice Lacking Native Insulin B9-23 Sequence", New York Academy of Sciences, 1079: pp. 122-129, 2006 (8 pages).
Nakayama, "Prime role for an insulin epitope in the development of type 1 diabetes in NOD mice", Nature Publishing Group, vol. 435, May 12, 2005, pp. 220-223 (4 pages).
Nakayama, "Priming and effector dependence on insulin B:9-23 peptide in NOD islet autoimmunity", The Journal of Clinical Investigation, vol. 117, No. 7, Jul. 2007, pp. 1835-1843 (9 pages).
McGraw-Hill Dictionary of Scientific and Medical Terms, 5th edition (1994), p. 41 (2 pages).
Stedman's Medical Dictionary (2000), p. 28 (2 pages).
Aucouturier, J., et al., "Montanide ISA 720 and 51: a new generation of water in oil emulsions as adjuvants for human vaccines", Expert Rev. Vaccines, 1(1), pp. 111-118, 2002 (8 pages).
Ferdinand, W., "The Enzyme Molecule", Department of Biochemistry, The University, Sheffield, Chapter 3, p. 82, 1976 (3 pages).
Orban et al., "Autoantigen-specific regulatory T cells induced in patients with type 1 diabetes mellitus by insulin B chain immunotherapy", Journal of Autoimmunity, vol. 34, pp. 408-415, 2010 (8 pages).

* cited by examiner

INSULIN B CHAIN AUTOANTIGEN COMPOSITION

RELATED APPLICATIONS

This application is a continuation of U.S. application Ser. No. 10/038,686, filed Jan. 4, 2002 now abandoned, which claims the benefit of U.S. Provisional Application Ser. No. 60/260,068, filed Jan. 5, 2001. The contents of both applications are incorporated herein by reference in their entirety.

BACKGROUND

Despite the significant progress that has been made in its treatment, diabetes represents a severe burden on the individual as well as society. Insulin dependent diabetes mellitus (Type 1 diabetes) is an autoimmune disease, where insulitis leads to the destruction of pancreatic β-cells. At the time of clinical onset of type 1 diabetes mellitus, significant number of insulin producing β cells are destroyed and only 15% to 40% are still capable of insulin production (McCulloch et al. (1991) *Diabetes* 40:673-679). β-cell failure results in a life long dependence on daily insulin injections and exposure to the acute and late complication of the disease. The natural history of the disease is that the remaining functional population of β-cells inevitably dies, rendering the patients dependent on exogenous insulin for life. Arrest or even the slow down of further destruction of β-cells would lead to prolonged remission period and delay the diabetes-related complications.

Insulin, which is a β-cell specific major protein and is also moderately immunogenic when used alone, has been shown in a pilot human trial to have the effect of delaying the development of diabetes mellitus (Keller et al. (1993) *Lancet* 341: 927-928). However, it must be injected daily over long periods of time to induce the desired effect. Also, the use of insulin implicates a concern about hypoglycemia and its sequels.

Reintroduction of autoantigen, such as insulin B chain, in incomplete Freund's adjuvant (IFA), has been used in animal models of diabetes, such as NOD mice (Muir et al. (1995) *J Clin Invest* 95:628-634; Orban et al. (1999) *Diabetes* 48 Supp.1:A216-A217; Ramiya et al. (1996) *J Autoimmun* 9:349-356).

SUMMARY OF THE INVENTION

In one aspect, the invention features a method for the prevention or treatment of an autoimmune disorder, e.g., rheumatoid arthritis, multiple sclerosis, or diabetes, e.g., type 1 diabetes. The methods include administering to a subject, e.g., a human, preferably a non-immunocompromised or non-immunosuppressed human, a composition, e.g., a vaccine, which contains an autoantigen and an oil-based carrier, e.g., an oil-based adjuvant, e.g., incomplete Freund's adjuvant (IFA), Montanide ISA (e.g., Montanide ISA51) or an equivalent composition. In preferred embodiments, the oil-based carrier or adjuvant, and preferably the composition, does not include a bacterial component, e.g., a mycobacterial component.

In a preferred embodiment, the subject is at risk for type 1 diabetes.

In another preferred embodiment, the subject exhibits autoimmunity, e.g., against a diabetes autoantigen.

In a preferred embodiment, the autoantigen is a diabetes type 1 autoantigen, e.g., an islet cell autoantigen.

In a preferred embodiment, the autoantigen is preproinsulin or an immunologically active fragment or variant thereof, e.g., human insulin A-chain, B-chain, C peptide or an immunologically active fragment or variant thereof, e.g., the autoantigen is a fragment of the sequence shown as SEQ ID NO:1.

In a preferred embodiment, the autoantigen is human insulin B-chain (amino acids 25-54 of SEQ ID NO:1) or an immunologically active fragment, or variant thereof.

In a preferred embodiment, the B-chain or fragment thereof is not recombinant. For example, the B-chain or immunogenic fragment or variant thereof is a synthetic peptide, e.g., the B-chain is made by solid-phase synthesis. In a preferred embodiment, the B-chain is solubilized in urea.

In another preferred embodiment, the autoantigen is GAD65 or an immunologically active fragment or variant thereof.

In another preferred embodiment, the autoantigen is islet tyrosine phosphatase ICA512/IA-2 or an immunologically active fragment, or variant thereof.

In a preferred embodiment, the autoantigen is HSP60 or an immunologically active fragment or variant thereof.

In a preferred embodiment, the autoantigen is carboxypeptidase H or an immunologically active fragment or variant thereof.

In another preferred embodiment, the autoantigen is peripherin or an immunologically active fragment or variant thereof.

In yet another preferred embodiment, the autoantigen is a ganglioside, e.g., GM1-2, GT3, GD3, GM-1 or an immunologically active fragment or variant thereof.

In a preferred embodiment, the immunologically active fragment or variant of an autoantigen described herein lacks one or more biological activity of the native autoantigen, but retains the ability to react with an autoantigen antibody. E.g., an insulin fragment or variant lacks a hypoglycaemic effect.

In a preferred embodiment, the composition is a pharmaceutical composition.

In a preferred embodiment, the composition is a vaccine.

In a preferred embodiment, the oil-based adjuvant is IFA, Montanide ISA (e.g., Montanide ISA51) or an equivalent composition.

In a preferred embodiment, the autoantigen or fragment or variant is not recombinant. For example, the autoantigen is a synthetic peptide, e.g., made by solid-phase synthesis.

In a preferred embodiment, the subject is not immunocompromised, e.g., the subject is not HIV positive or does not have AIDS.

In another aspect, the invention features methods for the prevention or treatment of diabetes mellitus. The methods include, optionally, identifying a subject, e.g., a human, in need of prevention or treatment of the autoimmune disorder; and administering to the subject a composition, e.g., a vaccine, comprising a diabetes type 1 autoantigen and an oil-based carrier, e.g., an oil-based adjuvant, e.g., IFA or other oil based adjuvant, e.g., Montanide ISA51 or an equivalent composition. In preferred embodiments, the oil-based carrier or adjuvant, and preferably the composition, does not include a bacterial component, e.g., a mycobacterial component.

In a preferred embodiment, the autoantigen is an islet cell autoantigen.

In a preferred embodiment, the autoantigen is preproinsulin or an immunologically active fragment thereof, e.g., human insulin A-chain, B-chain, C peptide or an immunologically active fragment or variant thereof, e.g., the autoantigen is a fragment of the sequence shown as SEQ ID NO:1.

In a preferred embodiment, the autoantigen is human insulin B-chain (amino acids 25-54 of SEQ ID NO:1) or an immunologically active fragment or variant thereof (e.g., residues 33-47 of SEQ ID NO:1). In a preferred embodiment, the B-chain or fragment thereof is not recombinant. For example, the B-chain or immunogenic fragment or variant thereof is a synthetic peptide, e.g., the B-chain is made by solid-phase synthesis. In a preferred embodiment, the B-chain is solubilized in urea.

In another preferred embodiment, the autoantigen is GAD65 or an immunologically active fragment or variant thereof.

In another preferred embodiment, the autoantigen is islet tyrosine phosphatase ICA512/IA-2 or an immunologically active fragment or variant thereof, e.g., amino acids 600-979 of SEQ ID NO:3 or an immunogenic fragment or variant thereof.

In a preferred embodiment, the autoantigen is HSP60 or an immunologically active fragment or variant thereof.

In a preferred embodiment, the autoantigen is carboxypeptidase H or an immunologically active fragment or variant thereof.

In another preferred embodiment, the autoantigen is peripherin or an immunologically active fragment or variant thereof.

In yet another preferred embodiment, the autoantigen is a ganglioside, e.g., GM1-2, GT3, GD3, GM-1 or an immunologically active fragment or variant thereof.

In a preferred embodiment, the autoimmune disorder is type 1 diabetes mellitus.

In a preferred embodiment, the autoantigen is human insulin B-chain.

In a preferred embodiment, the pharmaceutical composition is a vaccine.

In a preferred embodiment, the oil-based adjuvant is Montanide ISA (e.g., Montanide ISA51) or an equivalent composition.

In a preferred embodiment, the subject is not immunocompromised, e.g., the subject is not HIV positive or does not have AIDS.

In another aspect, the invention features a pharmaceutical composition, e.g., a vaccine, containing an autoantigen, e.g., a human autoantigen, e.g., a type 1 diabetes autoantigen, and an oil-based carrier, e.g., IFA or other oil based adjuvant, e.g., Montanide ISA (e.g., Montanide ISA51) or an equivalent composition. In preferred embodiments, the oil-based carrier or adjuvant, and preferably the composition, does not include a bacterial component, e.g., a mycobacterial component.

In a preferred embodiment, the autoantigen is a diabetes type 1 autoantigen, e.g., an islet cell autoantigen.

In a preferred embodiment, the autoantigen is preproinsulin or an immunologically active fragment thereof, e.g., human insulin A-chain, B-chain, C peptide or an immunologically active fragment or variant thereof, e.g., the autoantigen is a fragment of the sequence shown as SEQ ID NO:1.

In a preferred embodiment, the autoantigen is human insulin B-chain (amino acids 25-54 of SEQ ID NO:1) or an immunologically active fragment or variant thereof. In a preferred embodiment, the B-chain or fragment thereof is not recombinant. For example, the B-chain or immunogenic fragment or variant thereof is a synthetic peptide, e.g., made by solid-phase synthesis. In a preferred embodiment, the B-chain is solubilized in urea.

In another preferred embodiment, the autoantigen is GAD65 or an immunologically active fragment or variant thereof.

In another preferred embodiment, the autoantigen is islet tyrosine phosphatase ICA512/IA-2 or an immunologically active fragment or variant thereof, e.g., amino acids 600-979 of SEQ ID NO:3 or an immunogenic fragment or variant thereof.

In a preferred embodiment, the autoantigen is HSP60 or an immunologically active fragment or variant thereof.

In a preferred embodiment, the autoantigen is carboxypeptidase H or an immunologically active fragment or variant thereof.

In another preferred embodiment, the autoantigen is peripherin or an immunologically active fragment or variant thereof.

In yet another preferred embodiment, the autoantigen is a ganglioside, e.g., GM1-2, GT3, GD3, GM-1 or an immunologically active fragment or variant thereof.

In a preferred embodiment, the autoimmune disorder is type 1 diabetes mellitus.

In a preferred embodiment, the autoantigen is human insulin B-chain.

In a preferred embodiment, the pharmaceutical composition is a vaccine.

In a preferred embodiment, the adjuvant is Montanide ISA51 or an equivalent composition.

In a preferred embodiment, the immunologically active fragment or variant of an autoantigen described herein lacks one or more biological activity of the native autoantigen, but retains the ability to react with an autoantigen antibody. E.g., an insulin fragment or variant lacks a hypoglycaemic effect.

The invention also features a pharmaceutical composition, e.g., a vaccine, comprising a diabetes type 1 autoantigen and an oil-based carrier, e.g., IFA or other oil based adjuvant, e.g., Montanide ISA (e.g., Montanide ISA51), where the diabetes type 1 autoantigen is in a dosage sufficient to provide a therapeutic effect in a human. In preferred embodiments, the oil-based carrier or adjuvant, and preferably the composition, does not include a bacterial component, e.g., a mycobacterial component.

In a preferred embodiment, the autoantigen is preproinsulin or an immunologically active fragment thereof, e.g., human insulin A-chain, B-chain, C peptide or an immunologically active fragment or variant thereof, e.g., the autoantigen is a fragment of the sequence shown as SEQ ID NO:1.

In a preferred embodiment, the autoantigen is human insulin B-chain or an immunologically active fragment or variant thereof.

In a preferred embodiment, the B-chain is solubilized in urea.

In a preferred embodiment, the B-chain or fragment thereof is not recombinant. For example, the B-chain or immunogenic fragment or variant thereof is a synthetic peptide, e.g., the B-chain is made by solid-phase synthesis.

In a preferred embodiment, the B-chain is solubilized in urea In another preferred embodiment, the autoantigen is GAD65 or an immunologically active fragment or variant thereof. In another preferred embodiment, the autoantigen is islet tyrosine phosphatase ICA512/IA-2 or an immunologically active fragment or variant thereof.

In a preferred embodiment, the autoantigen is HSP60 or an immunologically active fragment or variant thereof.

In a preferred embodiment, the autoantigen is carboxypeptidase H or an immunologically active fragment or variant thereof.

In another preferred embodiment, the autoantigen is peripherin or an immunologically active fragment or variant thereof.

In yet another preferred embodiment, the autoantigen is a ganglioside, e.g., GM1-2, GT3, GD3, GM-1 or an immunologically active fragment or variant thereof.

In a preferred embodiment, the autoimmune disorder is type 1 diabetes mellitus.

In a preferred embodiment, the human insulin B-chain is between 30-70%, preferably between 40-60%, more preferably between 45-55% proportion weight by weight (w/w).

In a preferred embodiment, the IFA or other oil based adjuvant is present between 30-70%, preferably between 40-60%, more preferably between 45-55% proportion weight by weight (w/w).

In a preferred embodiment, the human insulin B-chain and the IFA or other oil based adjuvant are present in about a 50/50 weight by weight ratio.

In a preferred embodiment, the human insulin B-chain is denatured, e.g., solubilized in urea and DTT.

In a preferred embodiment, the pharmaceutical composition is free of contaminants, e.g., pyrogens.

In a preferred embodiment, the immunologically active fragment or variant of an autoantigen described herein lacks one or more biological activity of the native autoantigen, but retains the ability to react with an autoantigen antibody. E.g., an insulin fragment or variant lacks a hypoglycaemic effect.

In another aspect, the invention features kits for preventing or treating an autoimmune disorder, e.g., diabetes mellitus, or other autoimmune disorder described herein. The kits contain a human autoantigen, e.g., a diabetes autoantigen described herein, an oil based carrier, e.g., an oil-based adjuvant, e.g., IFA, or other oil based adjuvant, e.g., Montanide ISA (e.g., Montanide ISA51), and instructions indicating suitability for human use. In preferred embodiments, the oil-based carrier or adjuvant, and preferably the composition, does not include a bacterial component, e.g., a mycobacterial component.

In a preferred embodiment, the kits contain a diabetes type 1 autoantigen, e.g., a diabetes type 1 autoantigen described herein; IFA or other oil based adjuvant, e.g., Montanide ISA (e.g., Montanide ISA51),; and instructions indicating suitability for human use, e.g., to prevent, delay the clinical onset of, or treat type 1 diabetes in a human.

In a preferred embodiment, the autoantigen is a synthetic peptide.

In a preferred embodiment, the autoantigen is lyophilized.

In a preferred embodiment, the autoantigen is preproinsulin or an immunologically active fragment thereof, e.g., human insulin A-chain, B-chain, C peptide or an immunologically active fragment or variant thereof, e.g., the autoantigen is a fragment of the sequence shown as SEQ ID NO:1.

In a preferred embodiment, the autoantigen is human insulin B-chain (amino acids 25-54 of SEQ ID NO 1) or an immunologically active fragment or variant thereof. In a preferred embodiment, the B-chain or fragment thereof is not recombinant. For example, the B-chain or immunogenic fragment or variant thereof is a synthetic peptide, e.g., made by solid-phase synthesis. In a preferred embodiment, the B-chain is solubilized in urea.

In another preferred embodiment, the autoantigen is GAD65 or an immunologically active fragment or variant thereof.

In another preferred embodiment, the autoantigen is islet tyrosine phosphatase ICA512/IA-2 or an immunologically active fragment or variant thereof.

In a preferred embodiment, the autoantigen is HSP60 or an immunologically active fragment or variant thereof.

In a preferred embodiment, the autoantigen is carboxypeptidase H or an immunologically active fragment or variant thereof.

In another preferred embodiment, the autoantigen is peripherin or an immunologically active fragment or variant thereof.

In yet another preferred embodiment, the autoantigen is a ganglioside, e.g., GM1-2, GT3, GD3, GM-1 or an immunologically active fragment or variant thereof.

In a preferred embodiment, the adjuvant is Montanide ISA51 or an equivalent composition.

In a preferred embodiment, the immunologically active fragment or variant of an autoantigen described herein lacks one or more biological activity of the native autoantigen, but retains the ability to react with an autoantigen antibody. E.g., an insulin fragment or variant lacks a hypoglycaemic effect.

In another aspect, the invention features a delivery device, e.g., a syringe containing a composition described herein, e.g., an autoantigen, e.g., a diabetes type 1 autoantigen described herein; and an oil-based carrier, e.g., an adjuvant, e.g., IFA or other oil based adjuvant, e.g., Montanide ISA (e.g., Montanide ISA51). The delivery device, e.g., the syringe, can be configured for injection, e.g., intramuscular injection, in a human. In preferred embodiments, the oil-based carrier or adjuvant, and preferably the composition, does not include a bacterial component, e.g., a mycobacterial component.

In a preferred embodiment, the adjuvant in the syringe is Montanide ISA51 or an equivalent composition.

In another aspect, the invention features a composition, e.g., a pharmaceutical composition, made by the method of: combining human insulin B-chain or an immunologically active fragment or variant thereof and an oil-based carrier, e.g., an oil-based adjuvant, e.g., IFA, or other oil based adjuvant, e.g., Montanide ISA (e.g., Montanide ISA51), and emulsifying the insulin B-chain and oil-based adjuvant. In a preferred embodiment, human insulin B-chain and oil-based adjuvant are combined in a weight by weight ratio (w/w) of between 30/70 to 70/30, preferably between 40/60 to 60/40, more preferably about a 50/50 w/w ratio. In a preferred embodiment, emulsification is performed with a high pressure syringe. In preferred embodiments, the oil-based carrier or adjuvant, and preferably the composition, does not include a bacterial component, e.g., a mycobacterial component.

In a preferred embodiment, the adjuvant is Montanide ISA51 or an equivalent composition.

In a preferred embodiment, the pharmaceutical composition is a vaccine.

In a preferred embodiment, the immunologically active fragment or variant of B-chain lacks one or more biological activity of the native autoantigen (e.g., lacks hypoglycaemic effect), but retains the ability to react with an autoantigen antibody.

In another aspect, the invention features a method of enabling a health care provider to treat an autoimmune disorder in a human subject. The method includes providing the health care provider with a human autoantigen or immunogenic fragment or variant thereof (e.g., a diabetes type 1 autoantigen described herein); optionally providing the health care provider with an oil-based carrier, e.g., an oil-based adjuvant, e.g., IFA or other oil based adjuvant, e.g., Montanide ISA (e.g., Montanide ISA51); and providing the health care provider with instructions for use of the autoantigen to treat the subject. In preferred embodiments, the oil-based carrier or adjuvant, and preferably the composition, does not include a bacterial component, e.g., a mycobacterial component.

In a preferred embodiment, the autoantigen is preproinsulin, GAD 65, ICA512/IA-2, HSP60, carboxypeptidase H, peripherin, and ganglioside.

In a preferred embodiment, the autoantigen is human insulin B-chain or immunogenic fragment or variant thereof.

In a preferred embodiment, the autoantigen is a synthetic peptide.

In a preferred embodiment, the human diabetes autoantigen is lyophilized.

In a preferred embodiment, the adjuvant is IFA.

In a preferred embodiment, the adjuvant is Montanide ISA51 or an equivalent composition.

In a preferred embodiment, the subject is not immunocompromised, e.g., the subject is not HIV positive or does not have AIDS.

In another aspect, the invention features a method of preparing a diabetes type 1 composition, e.g., a vaccine. The method includes (a) solubilizing a diabetes type 1 autoantigen, e.g., preproinsulin or an immunologically active fragment or variant thereof, e.g., insulin B-chain or an immunogenically active fragment or variant thereof, in urea and (b) emulsifying the solubilized autoantigen, e.g., B-chain, with an oil-based carrier, e.g., an oil-based adjuvant, e.g., IFA or other oil based adjuvant, e.g., Montanide ISA (e.g., Montanide ISA51).

In a preferred embodiment, the B-chain or immunogenically active fragment, or variant thereof is a synthetic peptide.

In a preferred embodiment, the B-chain or immunogenically active fragment or variant thereof is solubilized in about 3 M to 5 M urea, preferably in about 3.5 M to 4.5 M urea, most preferably in about 4 M urea. Preferably, the B-chain is solubilized in the presence of a reducing agent, e.g., DTT or an equivalent reducing agent, e.g., 1 to 5 mg of DTT is added during the solubilization step.

In a preferred embodiment, the human insulin B-chain is present between 30-70%, preferably between 40-60%, more preferably between 45-55% proportion weight by weight (w/w) in the emulsification. In a preferred embodiment, the IFA is present between 30-70%, preferably between 40-60%, more preferably between 45-55% proportion w/w ratio. Most preferably, the human insulin B-chain and the IFA are present in a 50/50 w/w ratio.

In a preferred embodiment, emulsification is performed with high pressure sterile syringes.

In a preferred embodiment, the IFA is Montanide ISA51 or other IFA suitable for human use.

In another aspect, the invention features a method of evaluating the risk of onset of human type 1 diabetes in a subject. The method includes evaluating the levels of IFN-γ and/or IL-4 in a subject, e.g., serum IFN-γ and/or serum IL-4. The presence of serum IFN-γ and the absence of serum IL-4 correlates with a high incidence of developing diabetes. The presence of serum IL-4 (e.g., regardless of serum IFN-γ levels) correlates with a lower incidence of developing diabetes. IL-4 and IFN-γ serum levels can also be used, e.g., as markers to monitor the effect of a compound, e.g., an autoantigen vaccine described herein, on Th1/Th2 balance in the subject.

In a preferred embodiment, the levels of serum IFN-γ and/or serum IL-4 are evaluated by serum ELISA assay.

"Treatment" or "treating a subject" is defined as the application or administration of a therapeutic agent to a patient, or application or administration of a therapeutic agent to an isolated tissue or cell line from a patient, who has a disease, a symptom of disease or a predisposition toward a disease. Treatment can slow, cure, heal, alleviate, relieve, alter, remedy, ameliorate, improve or affect the disease, the symptoms of disease or the predisposition toward disease. For example, treatment of a subject, e.g., a human subject, with a composition described herein, can slow, improve, or stop the ongoing autoimmunity, e.g., a reaction against pancreatic β-cells, in a subject before, during, or after the clinical onset of type 1 diabetes.

An "oil-based carrier" as used herein is a composition that includes at least 10% by weight of a natural or synthetic oil suitable for administration to a human in conjunction with a therapeutic agent. In preferred embodiments, the carrier includes at least 20, 30, 50, 70, 80, 90, 95, 98, or 99% oil by weight. In some embodiments, the oil-based carrier can include less than 70, 60, 50, 40, 30 or 20% oil by weight. In preferred embodiments, the oil will be in the range of 10 to 95%, preferably 20 to 90% or 30 to 70% oil by weight. The oil should be chosen such that it provides for sustained release of a substance dispersed within it when administered to a subject. Suitable oils include mineral oil (e.g., Drakeol 6 VR light mineral oil), vegetable oil, squalene, or liquid paraffin. In some embodiments, the oil-based carrier can contain more than one type of oil. In some embodiments, the oil-based carrier can include an immune stimulator, e.g., an immunostimulating glucan, but it is much preferred that the oil-based carrier does not include an immune stimulator, e.g., an immunostimulating glucan, a bacterial component, e.g., a mycobacterial component. In a preferred embodiment, the oil-based carrier does not include an alum component.

While not wanting to be bound by theory, an oil based carrier is believed to work by triggering the immunocompetent cells, which are related to the inflammatory ability. An oil-based carrier can also act as an antigen vehicle and a slow release or long-term antigen presentation device. When injected into a subject, an oil-based carrier and antigen composition can form a depot of antigen at the injection site, thereby protecting the antigen from degradation. From this depot the antigen can be released slowly into the system and provides a prolonged antigen presentation as well as expanded total contact surface area and the attraction of inflammatory cells. Macrophages can digest most of the incorporated materials and present the processed antigens on their surface Oil based carriers should include an emulsifier or surfactant component. The emulsifier or surfactant (and the amount of emulsifier or surfactant) is chosen such that it facilitates the mixture or dispersion of a substance, e.g., an antigen preparation, with the oil. An oil-based carrier can include 0.1 to 50%, preferably 1 to 30%, more preferably 5 to 20% by weight of a surfactant or emulsifier. Examples of emulsifiers or surfactants include Arlacel A, mannide oleate (e.g., Montanide 80-mannide monooleate), anhydrous mannitol/oleic acid ester, polyoxyethylene or polyoxypropylene.

An "autoantigen" as used herein, is a protein that despite being a normal cell or tissue constituent, can be the target of a humoral or cell-mediated immune response in a subject. For example, diabetes type 1 autoantigens are typically normal protein constituents of pancreatic cells. An "immunologically active fragment" of an autoantigen described herein is an autoantigen in which one or more amino acid residues have been deleted and the fragment retains the ability to react with an autoantigen antibody or to stimulate the production of antibodies against the autoantigen. For example, an immunologically active fragment can be an autoantigen polypeptide in which residues have been successively deleted from the amino- and/or carboxyl-termini, while substantially retaining immunogenic activity. For example, insulin B-chain (amino acids 25-54 of SEQ ID NO: 1) is an immunologically active fragment of preproinsulin; a polypeptide that includes amino acids 33-37 of SEQ ID NO: 1 is an immunologically active fragment of B-chain; a polypeptide that includes amino acids from about 600 to 979 of SEQ ID NO:3 includes an immunologically active fragment of IA-2. In a preferred embodiment, the immunologically active fragment is a fragment of any of SEQ ID Nos:1-6. Preferred fragments lacks one or more biological activities of the native autoantigen, but retain the ability to react with an autoantigen antibody. E.g., a preferred insulin fragment or variant lacks a hypoglycaemic effect. Preferably, an immunologically active fragment of an autoantigen described herein is between 4 and 400 amino acid residues in length, more preferably between 10 and 300 amino acid residues in length, more preferably between 30 and 200 amino acid residues in length.

An "immunologically active variant" of an autoantigen described herein is an autoantigen that has been modified by addition, modification or substitution of one or more amino acid residues in the naturally occurring autoantigen and retains the ability to react with an autoantigen antibody or to stimulate the production of antibodies against the autoantigen. The variants described herein encompass allelic and polymorphic variants, and also muteins and fusion proteins that retain the ability to bind an autoantigen antibody or to produce an immune response against the autoantigen in a human. For example, up to 20%, preferably up to 10%, of the amino acid residues of an autoantigen can be replaced with substitute amino acids, so long as the variant retains the ability to bind autoantigen or produce an immune response against the autoantigen, e.g., in a human. A variant can also include an autoantigen or fragment thereof described herein in which one or more amino acids have been inserted or added, e.g., an autoantigen that has been coupled or fused to a carrier peptide. Also included are variants containing modifications, such as incorporation of unnatural amino acid residues, or phosphorylated, sulfonated, or biotinylated amino acid residues. Modifications of amino acid residues may also include aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine. Other modifications include the addition of other moieties, particularly those that may increase the immunogenicity of the autoantigen. Preferred variants lacks one or more biological activities of the native autoantigen, but retain the ability to react with an autoantigen antibody. E.g., a preferred insulin variant lacks a hypoglycaemic effect.

All publications cited herein are hereby incorporated by reference in their entirety. The details of one or more embodiments of the invention are set forth in the accompanying drawings and the description below. Other features, objects, and advantages of the invention will be apparent from the description and drawings, and from the claims.

DETAILED DESCRIPTION

The present invention relates to methods of preventing or treating an autoimmune disorder, e.g., Type 1 diabetes mellitus, in humans. The method includes administering to a patient a pharmaceutical composition, e.g., a vaccine, containing an autoantigen, e.g., a type 1 diabetes autoantigen described herein, in IFA, or other oil-based adjuvant, e.g., Montanide ISA51 or an equivalent composition. A preferred adjuvant includes an oil and an emulsifier. In a preferred embodiment, the vaccine can stop or slow down the ongoing autoimmunity, e.g., a reaction against pancreatic β-cells at the clinical onset of the disease. Although not wishing to be bound by theory, it is believed that the vaccine can alter the autoimmune process and stop autodestruction of the pancreatic β-cells.

Incomplete Freund's adjuvant (IFA) is a preferred delivery vehicle for the autoantigen in humans. The methods of the invention can prevent diabetes mellitus, or prevent or delay loss of residual β-cell mass, providing a longer remission period and delaying the onset of diabetes related, usually progressive, complications at a later stage of the life.

Autoantigens

Autoantibodies against insulin, glutamic acid decarboxylase (GAD) and other islet cell autoantigens, e.g., ICA 512/IA-2 protein tyrosine phosphatase, ICA12, ICA69, are frequently found in newly diagnosed diabetic patients. Thus, type 1 diabetes autoantigens useful in the methods of the invention include, e.g., preproinsulin or an immunologically active fragment thereof (e.g., insulin B-chain, A chain, C peptide or an immunologically active fragment thereof), and other islet cell autoantigens (ICA), e.g., GAD65, islet tyrosine phosphatase ICA512/IA-2, ICA12, ICA69 or immunologically active fragments thereof. Other type 1 diabetes autoantigens include HSP60, carboxypeptidase H, peripherin, gangliosides (e.g., GM1-2, GM3) or immunologically active fragments thereof. Any of the type 1 diabetes autoantigens described herein, or immunologically active fragments, analogs or derivatives thereof, are useful in the methods and compositions of the invention.

Autoantigens useful in treatment of other diseases include myelin proteins for prevention or treatment of multiple sclerosis or Type 1I collagen for prevention or treatment of rheumatoid arthritis.

Diabetes Autoantigens

Preproinsulin

The insulin mRNA is translated as a 110 amino acid single chain precursor called preproinsulin, and removal of its signal peptide during insertion into the endoplasmic reticulum generates proinsulin. Proinsulin consists of three domains: an amino-terminal B chain, a carboxy-terminal A chain and a connecting peptide in the middle known as the C peptide. Within the endoplasmic reticulum, proinsulin is exposed to several specific endopeptidases which excise the C peptide, thereby generating the mature form of insulin which consists of the A and B chain. Insulin and free C peptide are packaged in the Golgi into secretory granules which accumulate in the cytoplasm. The preproinsulin peptide sequence is as follows. MALWMRLLPL LALLALWGPD PAAAFVNQHL CGSHLVEALY LVCGERGFFY TPKTRREAED LQVGQVELGG GPGAGSLQPL ALEGSLQKRG IVEQCCTSIC SLYQLENYCN (SEQ ID NO:1)

Insulin A chain includes amino acids 90-110 of SEQ ID NO 1. B chain includes amino acids 25-54 of SEQ ID NO 1. The connecting sequence (amino acids 55-89 of SEQ ID NO 1) includes a pair of basic amino acids at either end. Proteolytic cleavage of proinsulin at these dibasic sequences liberates the insulin molecule and free C peptide, which includes amino acids 57-87 of SEQ ID NO 1. The human preproinsulin or an immunologically active fragment thereof, e.g., B chain or an immunogenic fragment thereof, e.g., amino acids 33-47 of SEQ ID NO:1 (corresponding to residues 9-23 of the B-chain), are useful as autoantigens in the methods and compositions described herein.

GAD65

Gad65 is a primary β-cell antigen involved in the autoimmune response leading to insulin dependent diabetes mellitus (Christgau et al. (1991) J Biol. Chem. 266(31):21257-64). The presence of autoantibodies to GAD65 is used as a method of diagnosis of type 1 diabetes. Gad65 is a 585 amino acid protein as follows (SEQ ID NO:2).

```
                                               (SEQ ID NO: 2)
MASPGSGFWS  FGSEDGSGDS  ENPGTARAWC  QVAQKFTGGI

GNKLCALLYG  DAEKPAESGG  SQPPRAAARK  AACACDQKPC

SCSKVDVNYA  FLHATDLLPA  CDGERPTLAF  LQDVMNILLQ

YVVKSFDRST  KVIDFHYPNE  LLQEYNWELA  DQPQNLEEIL

MHCQTTLKYA  IKTGHPRYFN  QLSTGLDMVG  LAADWLTSTA

NTNMFTYEIA  PVFVLLEYVT  LKKMREIIGW  PGGSGDGIFS

PGGAISNMYA  MMIARFKMFP  EVKEKGMAAL  PRLIAFTSEH

SHFSLKKGAA  ALGIGTDSVI  LIKCDERGKM  IPSDLERRIL

EAKQKGFVPF  LVSATAGTTV  YGAFDPLLAV  ADICKKYKIW

MHVDAAWGGG  LLMSRKHKWK  LSGVERANSV  TWNPHKMMGV

PLQCSALLVR  EEGLMQNCNQ  MHASYLFQQD  KHYDLSYDTG

DKALQCGRHV  DVFKLWLMWR  AKGTTGFEAH  VDKCLELAEY

LYNIIKNREG  YEMVFDGKPQ  HTNVCFWYIP  PSLRTLEDNE

ERMSRLSKVA  PVIKARMMEY  GTTMVSYQPL  GDKVNFFRMV

ISNPAATHQD  IDFLIEEIER  LGQDL
```

Islet Tyrosine Phosphatase IA-2

IA-2/ICA512), a member of the protein tyrosine phosphatase family, is another major autoantigen in type 1 diabetes (Lan et al. *DNA Cell Biol* 13:505-514, 1994). 70% of diabetic patients have autoantibodies to IA-2, which appear years before the development of clinical disease. The IA-2 molecule (SEQ ID NO:3, below) is 979 amino acids in length and consists of an intracellular, transmembrane, and extracellular domain (Rabin et al. (1994) J. Immunol. 152 (6), 3183-3188). Autoantibodies are typically directed to the intracellular domain, e.g., amino acids 600-979 of SEQ ID NO:3 and fragments thereof (Zhang et al. (1997) Diabetes 46:40-43; Xie et al. (1997) J Immunol 159:3662-3667). The amino acid sequence of IA-2 is as follows.

```
                                               (SEQ ID NO: 3)
MRRPRRPGGLGGSGGLRLLLCLLLLSSRPGGCSAVSAHGCLFDRRLCSHL

EVCIQDGLFGQCQVGVGQARPLLQVTSPVLQRLQGVLRQLMSQGLSWHDD

LTQYVISQEMERIPRLRPPEPRPRDRSGLAPKRPGPAGELLLQDIPTGSA

PAAQHRLPQPPVGKGGAGASSSLSPLQAELLPPLLEHLLLPPQPPHPSLS

YEPALLQPYLFHQFGSRDGSRVSEGSPGMVSVGPLPKAEAPALFSRTASK

GIFGDHPGHSYGDLPGPSPAQLFQDSGLLYLAQELPAPSRARVPRLPEQG

SSSRAEDSPEGYEKEGLGDRGEKPASPAVQPDAALQRLAAVLAGYGVELR

QLTPEQLSTLLTLLQLLPKGAGRNPGGVVNVGADIKKTMEGPVEGRDTAE

LPARTSPMPGHPTASPTSSEVQQVPSPVSSEPPKAARPPVTPVLLEKKSP

LGQSQPTVAGQPSARPAAEEYGYIVTDQKPLSLAAGVKLLEILAEHVHMS

SGSFINISVVGPALTFRIRHNEQNLSLADVTQQAGLVKSELEAQTGLQIL

QTGVGQREEAAAVLPQTAHSTSPMRSVLLTLVALAGVAGLLVALAVALCV

RQHARQQDKERLAALGPEGAHGDTTFEYQDLCRQHMATKSLFNRAEGPPE

PSRVSSVSSQFSDAAQASPSSHSSTPSWCEEPAQANMDISTGHMILAYME

DHLRNRDRLAKEWQALCAYQAEPNTCATAQGEGNIKKNRHPDFLPYDHAR
```

```
IKLKVESSPSRSDYINASPIIEHDPRMPAYIATQGPLSHTIADFWQMVWE

SGCTVIVMLTPLVEDGVKQCDRYWPDEGASLYHVYEVNLVSEHIWCEDFL

VRSFYLKNVQTQETRTLTQFHFLSWPAEGTPASTRPLLDFRRKVNKCYRG

RSCPIIVHCSDGAGRTGTYILIDMVLNRMAKGVKEIDIAATLEHVRDQRP

GLVRSKDQFEFALTAVAEEVNAILKALPQ
```

ICA12

ICA 12 (Kasimiotis et al. (2000) Diabetes 49(4):555-61; Gen bank Accession No. AAD16237; SEQ ID NO:4) is one of a number of islet cell autoantigens associated with diabetes. The sequence of ICA12 is as follows.

```
                                               (SEQ ID NO: 4)
MSMRSPISAQ  LALDGVGTMV  NCTIKSEEKK  EPCHEAPQGS

ATAAEPQPGD  PARASQDSAD  PQAPAQGNFR  GSWDCSSPEG

NGSPEPKRPG  ASEAASGSQE  KLDFNRNLKE  VVPAIEKLLS

SDWKERFLGR  NSMEAKDVKG  TQESLAEKEL  QLLVMIHQLS

TLRDQLLTAH  SEQKNMAAML  FEKQQQQMEL  ARQQQEQIAK

QQQQLIQQQH  KINLLQQQIQ  QVNMPYVMIP  AFPPSHQPLP

VTPDSQLALP  IQPIPCKPVE  YPLQLLHSPP  APVVKRPGAM

ATHHPLQEPS  QPLNLTAKPK  APELPNTSSS  PSLKMSSCVP

RPPSHGGPTR  DLQSSPPSLP  LGFLGEGDAV  TKAIQDARQL

LHSHSGALDG  SPNTPFRKDL  ISLDSSPAKE  RLEDGCVHPL

EEAMLSCDMD  GSRHFPESRN  SSHIKRPMNA  FMVWAKDERR

KILQAFPDMH  NSSISKILGS  RWKSMTNQEK  QPYYEEQARL

SRQHLEKYPD  YKYKPRPKRT  CIVEGKRLRV  GEYKALMRTR

RQDARQSYVI  PPQAGQVQMS  SSDVLYPRAA  GMPLAQPLVE

HYVPRSLDPN  MPVIVNTCSL  REEGEGTDDR  HSVADGEMYR

YSEDEDSEGE  EKSDGELVVL  TD
```

ICA69

ICA69 is another autoantigen associated with type 1 diabetes (Pietropaolo et al. J Clin Invest 1993; 92:359-371). The amino acid sequence of ICA69 is as follows.

```
                                               (SEQ ID NO: 5)
MSGHKCSYPW  DLQDRYAQDK  SVVNKMQQRY  WETKQAFIKA

TGKKEDEHVV  ASDADLDAKL  ELFHSIQRTC  LDLSKAIVLY

QKRICFLSQE  ENELGKFLRS  QGFQDKTRAG  KMMQATGKAL

CFSSQQRLAL  RNPLCRFHQE  VETFRHRAIS  DTWLTVNRME

QCRTEYRGAL  LWMKDVSQEL  DPDLYKQMEK  FRKVQTQVRL

AKKNFDKLKM  DVCQKVDLLG  ASRCNLLSHM  LATYQTTLLH

FWEKTSHTMA  AIHESFKGYQ  PYEFTTLKSL  QDPMKKLVEK

EEKKKINQQE  STDAAVQEPS  QLISLEEENQ  RKESSSFKTE

DGKSILSALD  KGSTHTACSG  PIDELLDMKS  EEGACLGPVA

GTPEPEGADK  DDLLLLSEIF  NASSLEEGEF  SKEWAAVFGD
```

-continued
```
GQVKEPVPTM ALGEPDPKAQ TGSGFLPSQL LDQNMKDLQA

SLQEPAKAAS DLTAWFSLFA DLDPLSNPDA VGKTDKEHEL

LNA
``` glima38

Glima 38 is a 38 kDa islet cell membrane autoantigen which is specifically immunoprecipitated with sera from a subset of prediabetic individuals and newly diagnosed type 1 diabetic patients. Glima 38 is an amphiphilic membrane glycoprotein, specifically expressed in islet and neuronal cell lines, and thus shares the neuroendocrine expression patterns of GAD65 and IA2 (Aanstoot et al., J Clin Invest. 1996 Jun. 15; 97(12):2772-2783).

Heat Shock Protein 60 (HSP60)

HSP60, e.g., an immunologically active fragment of HSP60, e.g., p 277 (see Elias et al., *Eur J Immunol* 1995 25(10):2851-7), can also be used as an autoantigen in the methods and compositions described herein. Other useful epitopes of HSP 60 are described, e.g., in U.S. Pat. No. 6,110,746.

Carboxypeptidase H

Carboxypeptidase H has been identified as an autoantigen, e.g., in pre-type 1 diabetes patients (Castano et al. (1991) J Clin Endocrinol Metab 73(6):1197-201; Alcalde et al. J Autoimmun. 1996 August; 9(4):525-8.). Therefore, carboxypeptidase H or immunologically reactive fragments thereof (e.g., the 136-amino acid fragment of carboxypeptidase-H described in Castano, supra) can be used in the methods and compositions described herein.

Peripherin

Peripherin is a 58 KDa diabetes autoantigen identified in nod mice (Boitard et al. (1992) Proc Natl Acad Sci USA 89(1):172-6. The human peripherin sequence is shown as SEQ ID NO:6, below.

```
                                              (SEQ ID NO: 6)
MSHHPSGLRA GFSSTSYRRT FGPPPSLSPG AFSYSSSSRF

SSSRLLGSAS PSSSVRLGSF RSPRAGAGAL LRLPSERLDF

SMAEALNQEF LATRSNEKQE LQELNDRFAN FIEKVRFLEQ

QNAALRGELS QARGQEPARA DQLCQQELRE LRRELELLGR

ERDRVQVERD GLAEDLAALK QRLEEETRKR EDAEHNLVLF

RKDVDDATLS RLELERKIES LMDEIEFLKK LHEEELRDLQ

VSVESQQVQQ VEVEATVKPE LTAALRDIRA QYESIAAKNL

QEAEEWYKSK YADLSDAANR NHEALRQAKQ EMNESRRQIQ

SLTCEVDGLR GTNEALLRQL RELEEQFALE AGGYQAGAAR

LEEELRQLKE EMARHLREYQ ELLNVKMALD IEIATYRKLL

EGEESRISVP VHSFASLNIK TTVPEVEPPQ DSHSRKTVLI

KTIETRNGEQ VVTESQKEQR SELDKSSAHS Y
```

Gangliosides

Gangliosides can also be useful autoantigens in the methods and compositions described herein. Gangliosides are sialic acid-containing glycolipids which are formed by a hydrophobic portion, the ceramide, and a hydrophilic part, i.e. the oligosaccharide chain. Gangliosides are expressed, inter alia, in cytosol membranes of secretory granules of pancreatic islets. Auto-antibodies to gangliosides have been described in type 1 diabetes, e.g., GM1-2 ganglioside is an islet autoantigen in diabetes autoimmunity and is expressed by human native β cells (Dotta et al. Diabetes. 1996 September; 45(9): 1193-6). Gangliosides GT3, GD3 and GM-1 are also the target of autoantibodies associated with autoimmune diabetes (reviewed in Dionisi et al. Ann Ist Super Sanita 1997; 33(3):433-5). Ganglioside GM3 participates in the pathological conditions of insulin resistance (Tagami et al. J Biol Chem 2001 Nov. 13; online publication ahead of print).

Multiple Sclerosis Autoantigens

Autoantigens thought to be involved in multiple sclerosis (MS) include myelin basic protein, myelin oligodendrocyte glycoprotein, and human transaldolase.

Rheumatoid Arthritis Autoantigens

Collagen type 1I and cartilage proteins YKL-39 (Sekine et al. (2001) Annals of the Rheumatic Diseases 60:49-54) and YKL-40 (Kawasaki et al. (2001) J Rheumatol 28:341-345) have been reported to be autoantigens in rheumatoid arthritis.

Reintroduction of autoantigen in autoimmune disease can generate protective antigen-specific cell mediated immunity. A number of regulatory mechanisms differentially regulate the autoagressive Th1 and protective Th2 cell response (the two subsets of T helper cells) in mice and human alike. Th1 and Th2 have distinct and defined cytokine secretion profiles. The antigen activated Th1 (autoagressive) cells release IL-2 and IFN-γ, which inhibit the Th2 (protective) cell production of IL-4 and IL-10. Insulin B-chain in IFA has been shown to reduce IFN-γ (Th1) expression and reduce insulitis (Muir et al. (1995) *J Clin Invest* 95:628-634; Orban et al. (1999) *Diabetes* 48 Supp.1:A216-A217). Nasal administration of GAD65 also leads to change in Th1/Th2 balance in favor of Th2 'protective' cells response (Tian et al. (1996) *J Exp Med* 183:1561-1567). GAD in incomplete Freund's adjuvant in NOD mice leads to shift of Th1/Th2 balance toward the production of Th2 related cytokines like IL-4 and IL-10 (Sai et al. (1996) *Clin Exp Immunol* 105:330-337). Secretion of IgG1, IgG4 and IgE antibodies are preferentially stimulated by conditions leading to selective activation of Th2 lymphocytes (IL-4, IL-10 and the absence of IFN-gamma).

There are many autoantigens considered to be important in human Type 1 diabetes mellitus. Several data suggest that insulin is a major antigen playing roles in the pathogenesis of the disease (Muir et al. (1993) *Diabetes Metab Rev* 9:279-287). Insulin, a β-cell specific major protein is moderately immunogenic when used alone, and has been shown in a pilot human trial to have the effect of delaying the development of diabetes mellitus (Keller et al. (1993) *Lancet* 341:927-928). However, it must be injected daily over long periods of time to induce the desired effect. When insulin is used in humans, there is always a major concern about hypoglycemia and its sequels.

Immunogenic fragments or variants of insulin or preproinsulin lacking hypoglycaemic effect are a safe choice for human use. For example, insulin B-chain (or immunogenic fragments and variants thereof) can be used as an immune modulator to prevent or delay further loss of functional, residual β-cell mass, after the clinical onset of Type 1 diabetes in humans, without hypoglycaemic effect. The reintroduction of autoantigen, e.g., insulin B-chain, in human subjects can act to change to autoimmune process triggering a protective immune response. The Th1/Th2 balance can change in favor of a protective Th2 type cell response.

Human insulin B-chain for human vaccine use can be made by a standard solid-phase peptide synthesis (Example 1). A procedure for effective solubilization of the insulin B-chain is described herein (Example 2).

Changes in autoantibody titers and in GAD65AB isotypes reflecting the effect of autoantigen vaccination can be used to characterize the regression in autoimmune process in diabetic or prediabetic patients. In addition, there will be changes in stimulated cytokine profile (in favor of Th2-cells) correlating with the effect of the autoantigen vaccination, which later may be used as cellular marker for regression of autoimmunity in Type 1 diabetes mellitus.

Animal Studies

To test the efficacy of autoantigens in IFA, NOD mice were vaccinated with human recombinant GAD65 (300 µg/mice) in IFA (total volume 0.1 ml), human insulin B-chain (20.1 µg/mice) in IFA (total volume 0.1 ml) and sham protein (Lysozyme, 200 µg/mice) in IFA (total volume 0.1 ml) sc. in the inguinal areas at 3, 5 and 7 weeks of age. At 9 weeks of age the treated mice were sacrificed and their splenocytes ($1.0 \times 10^7$ cells) were cotransfered with splenocytes from 9 weeks old untreated NOD mice ($1.0 \times 10^7$ cells) into 9-11 weeks old NOD scid/scid mice (16 mice/group; total $2.0 \times 10^7$ cells/mice). Control group received splenocytes ($2.0 \times 10^7$ cells/mice) from untreated NOD mice. By the $75^{th}$ day after adoptive transfer all the scid/scid mice, recipients of splenocytes from the control and the sham protein vaccinated donor mice developed diabetes. 4/16 scid/scid mice, recipient of splenocytes from the GAD and 9/16 from the B-chain treated donor mice cotransfered with untreated mice splenocytes became diabetic ($p=0.0001$ and $p=0.0005$ respectively compared to the sham protein vaccinated group).

Histological studies were performed on the pancreases of the vaccinated mice at the time of adoptive transfer. The insulitis were graded on a 0-4 scale as previously described (Charlton et al. (1989) Diabetes 38:441-447). The mean insulitis scores were 1.31 in the GAD65 and 1.20 in B-chain treated groups meanwhile 2.64 in the sham protein treated and 2.71 in the control group ($p=0.0001$ for both GAD65 and B-chain vaccinated groups compare to sham protein treated mice).

These data show that immunization with a diabetes type 1 autoantigen, e.g., insulin B-chain or GAD65 protein, in IFA significantly reduces the incidence of diabetes in NOD scid/scid adoptive transfer model. The vaccines generated changes in the immune competent cells, which actively suppress the capacity of T-cells from prediabetic untreated donors to transfer the disease adoptively. The vaccination with these autoantigens also reduced insulitis in NOD mice. Sham protein in IFA was not effective, thus the intervention is antigen specific. Adjuvant enhanced autoantigen vaccination, e.g., with insulin B-chain or GAD65, actively suppressed the ongoing autoimmunity in mice thus provides diabetes-specific therapeutic intervention. Similar data on a different preparation of insulin B-chain have been reported by Muir et al. (1995, J. Clin. Invest. 95:628-634). Data on safety for human are summarized herein below.

Human Studies

Assays were developed to measure human GAD65 autoantibody isotypes. The data indicate that individuals with diabetes autoimmunity, but long diabetes-free follow up have a higher Th2 related GAD65 specific IgG isotypes measured by IgG1/IgG2 or by IgG1+IgG4/IgG2+IgG3 ratios then the aged matched newly diagnosed patients with Type 1 diabetes mellitus ($1.15 \pm 0.08$ SE vs.$0.76 \pm 0.09$ SE $p=0.006$ and $1.11 \pm$SE vs. $0.78 \pm 0.07$ SE $p=0.002$ respectively). This is indirect evidence that Th1/Th2 balance is at play in the pathogenesis of human Type 1 diabetes and consistent with Th1 dominance driving towards diabetes meanwhile Th2 activity contra-acts this process. This marker can be used to monitor the effect of the IFA enhanced autoantigens on the Th1/Th2 balance.

Many years before clinical onset of Type 1 diabetes, islet cell antibodies (ICA) can be detected. A subgroup of these ICA-positive individuals does not develop diabetes after long-term follow-up. We have studied 17 such ICA positive individuals with an average of 8.8 (3.7 to 29.2) years diabetes-free observation period. Fifteen have two or more samples collected at different time, from 1.6 to 8.2 years. All patients have autoantibodies against GAD65 human recombinant protein (positive index>0.1), 15/17 in high titer (index>0.5). This is significant increase compared to 19 ICA positive patients with diabetes (10/19 GAD65 positive index>0.5-high titer, $p=0.01$). They were also positive for IA2 or insulin autoantibodies. We have further studied this group of high-risk for Type 1 diabetes, non-progressors. CD4– CD8– double negative V$\alpha$24J$\alpha$Q$^+$ T cells were isolated from these individuals and 33 clones raised secreted IL-4 and IFN-gamma on stimulation with anti-CD3. This secretory pattern, which was similar to healthy controls, was in sharp contrast to patients with new onset Type 1 diabetes. None of the 56 clone tested from newly diagnosed patients with Type 1 diabetes secreted IL-4, thus showing an extreme Th1 bias. Seven of the 14 high-risk for Type 1 diabetes, non-progressor individuals had IL-4 level>1 ng/ml detectable by ELISA in their serum. When compared to either healthy or new onset Type 1 diabetes mellitus patients the frequency of serum IL-4 positive individuals was significantly elevated in the non-progressor group. Consequently, we examined serum levels of IL-4 and IFN-$\gamma$ activity using ELISA in subjects at high risk for developing Type 1 diabetes mellitus and correlated the results with disease outcome. A total of 1100 archived serum samples from 443 diabetes-free first degree relatives of patients with Type 1 diabetes mellitus were studied; 95 developed Type 1 diabetes during follow-up. Serum IL-4 and IFN-$\gamma$ by ELISA and additional autoantibodies for GAD65 and for IA2 were measured. Subjects with serum IFN-$\gamma$ ELISA activity (without IL-4 ELISA activity) levels had a significantly higher incidence of developing diabetes after five years (74.0% vs. cytokine negatives $p=0.03$)), while subjects with serum IL-4 ELISA pattern, regardless of IFN-$\gamma$ ELISA status, had a significantly lower incidence of developing diabetes (17.3% vs. cytokine negatives $p=0.003$).

Thus, levels of serum ELISA IL-4 and IFN-$\gamma$ activities are predictors of the onset of human Type 1 diabetes. We found that serum autoantibodies are independent markers for risk assessment in Type 1 diabetes.

These cellular (CD4– CD8– double negative V$\alpha$24J$\alpha$Q$^+$ T cells) and humoral (IL-4 and IFN-gamma ELISA serum levels) markers described herein can be used to monitor the effect of the IFA enhanced autoantigens on the Th1/Th2 balance.

Oil-Based Adjuvants

An oil-based adjuvant typically consists of two components: (1) an oil, and (2) an emulsifier or surfactant, mixed with water. Suitable oils and emulsifiers are known in the art. For example, the oil can be mineral oil, vegetable oil, squalene or liquid paraffin. The emulsifier or surfactant can be, e.g., Arlacel A, mannide oleate, anhydrous mannitol/oleic acid ester, polyoxyethylene or polyoxypropylene. Exemplary oil-based adjuvants include conventional IFA, Montanide ISA adjuvants, or Hunter's TiterMax adjuvant. In preferred embodiments, the adjuvant includes 20 to 95%, preferably 30 to 90%, more preferably 40 to 70% by weight of an oil phase, and 0.1 to 50%, preferably 1 to 30%, more preferably 5 to 20% by weight of a surfactant or emulsifier. Various types of oil-based adjuvants are described, e.g., in U.S. Pat. Nos. 5,814,321, 6,299,884, 6,235,282, 5,976,538, 5,904.

IFA is typically a mixture of a non-metabolizable oil (e.g., mineral oil), a surfactant (e.g., Arlacel A). Unlike Complete Freund's Adjuvant (CFA), IFA does not contain a bacterial component, e.g., mycobacteria. The first large-scale vaccinations using IFA in humans took place on US military personnel (Davenport (1968) *Ann Allergy* 26:288-292; Beebe et al. (1972) *Am J Epidemiol* 95:337-346; Salk & Salk (1977) *Science* 195:834-847). The findings were essentially negative with respect to malignancy, allergic diseases and collagenosis, but there was evidence that some men had a cyst like reaction at the site of inoculation. From these experiments, IFA was regarded by some as unsuitable for human purposes, although it has remained widely used in animal research. In recent years, newer forms of IFA have been shown safe for human use in HIV immunotherapy or therapeutic vaccinations (Turner et al. (1994) *AIDS* 8:1429-1435; Trauger et al. (1995) *J Acquir Immune Defic Syndr Hum Retrovirol* 10 Supp2:S74-82; Trauger et al. (1994) *J Infect Dis* 169:1256-1264).

Montanide ISA Adjuvants (Seppic, Paris, France) are a group of oil/surfactant based adjuvants in which different surfactants are combined with either a non-metabolizable mineral oil, a metabolizable oil, or a mixture of the two. They are prepared for use as an emulsion with aqueous Ag solution. The surfactant for Montanide ISA 50 (ISA=Incomplete Seppic Adjuvant) is mannide oleate, a major component of the surfactant in Freund's adjuvants. The surfactants of the Montanide group undergo strict quality control to guard against contamination by any substances that could cause excessive inflammation, as has been found for some lots of Arlacel A used in Freund's adjuvant. The various Montanide ISA group of adjuvants are used as water-in-oil emulsions, oil-in-water emulsions, or water-in-oil-in-water emulsions. The different adjuvants accommodate different aqueous phase/oil phase ratios, because of the variety of surfactant and oil combinations.

Hunter's TiterMax (CytRx Corp., Norcross, Ga.) is an oil/surfactant-based adjuvant prepared as a water-in-oil emulsion in a manner similar to that used for conventional Freund's adjuvants. However, it uses a metabolizable oil (squalene) and a nonionic surfactant that has good protein antigen-binding capacity as well as adjuvant activity. The adjuvant activity may relate, in part, to the surfactant's ability to activate complement and bind complement components, as this helps target the Ag to follicular dendritic cells in the spleen and lymph nodes. The surfactant used in the commercially available adjuvant is one of a number of synthetic nonionic block copolymers of polyoxyethylene and polyoxypropylene developed by Hunter (Hunter et al., 1991 *Vaccine* 9:250-256). The utilization of copolymer-coated microparticles to stabilize the emulsion permits formation of stable emulsions with less than 20% oil, an important factor in minimizing total adjuvant injected.

An adjuvant can be used with antigens to elicit cell-mediated immunity and the production of antibodies of protective isotypes (IgG2a in mice and IgG1 in primates). Different types of adjuvants share similar side effects, such as a reaction at the injection site and pyrogenicity. Alum, a commonly used adjuvant for human vaccine also produces an appreciable granulomatous response at the injection site (Allison & Byars (1991) *Mol Immunol* 28:279-284). The mode of action of an incomplete Freund's adjuvant can involve non-specific as well as specific immune responses. IFA seems to work by triggering the immunocompetent cells, which are related to the inflammatory ability. IFA also acts as an antigen vehicle and a slow release or long-term antigen presentation device. Injecting a patient with an IFA and antigen compound, it forms a depot of antigen at the injection site, thereby protecting the antigen from degradation. From this depot the antigen is released slowly into the system and provides a prolonged antigen presentation as well as expanded total contact surface area and the attraction of inflammatory cells. Macrophages digest most of the incorporated materials and present the processed antigens on their surface.

The specific enhancing effect of the IFA on the antigen immunogenicity has been found to lead to increased humoral immunity (preferentially protective antibody production; IgG1 in humans and IgG2a in mice) and to elicit specific cell mediated immunity (preferentially Th2 type). Specifically, human recombinant insulin B-chain in IFA results in Th2 cytokine pattern in NOD mice islets (Ramiya et al. (1996) *J Autoimmun* 9:349-356). IFA is unique among adjuvants tried for diabetes prevention in animal models. Ramiya and coworkers (supra) concluded that both alum and DPT as adjuvants have 'non-specific' protective effects unrelated to the antigen used, while IFA is the only one with antigen specific protective effect for diabetes prevention in animals.

IFA, preferably an IFA approved for human use, e.g., Montanide (e.g., Montanide ISA51, Seppic Inc., France) or an equivalent composition, is a preferred adjuvant for use in the methods and vaccines described herein. Montanide ISA51 has shown no systemic or significant local side effects in our animal studies.

Toxicology and Safety

A comprehensive toxicology/safety study on the vaccine described herein was performed. Intramuscular injection of the insulin B-chain/IFA vaccine on each of days 1, 7 and 14 to male BBDP/WOR and Sprague-Dawley rats at dose levels of 100 and 500 µg/rat, followed by a 14 day observation period had no toxicologically significant effects on clinical observation, body weights, food consumption, clinical pathology (hematology, coagulation, and clinical chemistry) and organ weights. Macroscopic (all animals) and microscopic (BBDP/WOR rats in low dose, high dose and vehicle control groups) evaluation showed injection site changes, including granulomatous inflammation attributable to the vehicle article.

The diabetes prone BBDP/WOR rats (the only other animal model of Type 1 diabetes apart from the NOD mice) received the insulin B-chain vaccine at a diabetes and insulitis free period of their life and neither the low dose nor the high dose precipitated early insulitis or diabetes.

Serum samples from the BBDP/WOR rats (6 rats/groups) were analyzed for insulin antibodies. There was a significant difference between the vehicle control vs. 100 µg insulin B-chain/rat and 500 µg insulin B-chain/rat doses (23.6 µU/ml+3.9SE vs. 37.9 µU/ml+4.5SE and 44.5 µU/ml+3.3SE; significance p=0.03 and p=0.002 respectively; no significant difference between low and high dose groups in insulin antibody titers).

The vaccine was also analyzed for pyrogens as per the standard USP method (UPS 23<151>) and meets the requirements for absence of pyrogens.

Because we have used IFA approved for human use, this intervention strategy can be directly applied in human diabetes.

Study 1

In our animal study where we used IFA with human insulin B-chain or with human GAD65 protein, the mice were carefully observed for any adverse effect. The feeding pattern, activity, behavior as well as site of injection for local reaction were regularly monitored by the sponsor-investigator and by the research assistant and no abnormality was detected throughout of the study. The mice were vaccinated three times and all three vaccinations were well tolerated without any detectable side effects (general—feeding pattern, activity, behavior; or local—local reaction at site of injection). At the time of sacrifice, after 9 weeks the internal organs as well the vaccination sites were observed by the sponsor-investigator and no abnormality was found (any induration, swelling redness or pain).

Study 2

A second comprehensive toxicology/safety study was executed under GLP conditions in an independent FDA inspected contract laboratory (ITR Laboratories Canada Inc.). The study was designed in consultation with GAD Consulting Services and was presented to the FDA prior initiation. It was deemed to be satisfactory to answer the outstanding questions of safety for this vaccine in humans. In brief, intramuscular injection of test article on each of Days 1, 7 and 14 to male BBDP/WOR and Sprague-Dawley rats at dose levels of 100 and 500 μg/rat, followed by a 14 day observation period had no toxicologically significant effects on clinical observation, body weights, food consumption, clinical pathology (hematology, coagulation, and clinical chemistry) and organ weights. Macroscopic (all animals) and microscopic (BBDP/WOR rats in low dose, high dose and vehicle control groups) evaluation showed injection site changes, including granulomatous inflammation attributable to the vehicle article.

The diabetes prone BBDP/WOR rats (the only other animal model of Type 1 diabetes apart from the NOD mice) received the IBC (insulin B-chain) vaccine at a diabetes and insulitis free period of their life and neither the low dose nor the high dose precipitated early insulitis or diabetes.

Serum samples from the BBDP/WOR rats (6 rats/groups) were analyzed for insulin antibodies. There was a significant difference between the vehicle control vs. 100 μg insulin B-chain/rat and 500 μg insulin B-chain/rat doses (23.6 μU/ml+3.9SE vs. 37.9 μU/ml+4.5SE and 44.5 μU/ml+3.3SE; significance p=0.03 and p=0.002 respectively; no significant difference between low and high dose groups in insulin antibody titers). The IBC vaccine was prepared fresh before injecting the animals. The preparations were sampled on Day 1 and Day 14.

The vaccine was also analyzed for pyrogens as per the standard USP method (UPS 23<151>) and been reported as meeting the requirements for absence of pyrogenes.

Many interventions used in NOD mice can not be considered in humans. In the results described herein, IFA approved for human use has been used, thus these intervention strategies can be directly applied in human diabetes. The IFA is safe and effective in humans. IFA is currently used in HIV and other vaccination trials (peptide-based melanoma vaccine at Univ. Virginia) approved by FDA.

Potential local side effects are similar to any commonly used adjuvant vaccinations (alum is currently used in human vaccines) and can include induration, moderate pain and low-grade fever. The injections can be given in small volume (1 ml) in deep intramuscular space, thus minimizing the local side effects.

Administration of Vaccines

Immunogenic compositions and vaccines may be administered parenterally, by injection subcutaneously, or intramuscularly. A preferred mode of administration is intramuscularly. For example, the vaccine described herein can be given as an intramuscular injection, preferably a deep intramuscular injection, in a small volume, e.g., 1 ml. The vaccine can be administered once, or more than once. It can be given before, or shortly after the onset of Type 1 diabetes mellitus.

Alternatively, the immunogenic compositions formed according to the present methods, may be formulated and delivered in a manner to evoke an immune response at a mucosal surface. Thus, the immunogenic composition may be administered by, e.g., nasal or oral (intragastric) routes. Other modes of administration include suppositories and oral formulations.

The vaccines described herein can be administered in a manner compatible with the dosage formulation, and in such amount as will be therapeutically effective, protective and immunogenic. The autoantigen in the vaccine is preferably a synthetic peptide or peptide variant as opposed to a recombinant peptide or protein which is more likely to have impurities and contaminants. The quantity to be administered depends on the subject to be treated, including, for example, the capacity of the individual's immune system to synthesize antibodies, the degree of protection desired, and if needed, to produce a cell-mediated immune response. Precise amounts of active ingredient required to be administered depend on the judgment of the practitioner. However, suitable dosage ranges are readily determinable by one skilled in the art and may be of the order of micrograms of the active ingredient(s) per vaccination. Suitable regimes for initial administration and booster doses are also variable, but may include an initial administration followed by subsequent administrations. The dosage may also depend on the route of administration and will vary according to the size of the host. For example, 2 mg of human insulin B chain solution can be administered to an adult human. The concentration of the active ingredient protein in an immunogenic composition according to the invention is in general about 1 to 95%.

A vaccine can also contain an adjuvant, e.g., an oil based adjuvant, e.g., IFA. Preferably, the vaccine contains an IFA suitable and approved for human use, e.g., Montanide ISA 51 or an equivalent composition.

The vaccines are prepared under conditions suitable for human administration. Preferably, the vaccine injection is prepared as an emulsion immediately before administration, under sterile conditions, by using high pressure sterile syringes as a 50/50 (w/w) emulsion of insulin B-chain/IFA.

The methods and vaccines described herein can be used to prevent the onset of an autoimmune disease, e.g., diabetes mellitus. The methods and vaccines can also be used to arrest the autoimmune destruction of tissue, e.g., pancreatic β cells. The methods and vaccines are useful to arrest the autoimmune destruction, even at a late stage. For example, at the time of clinical onset of type 1 diabetes mellitus, significant number of insulin producing β cells are destroyed but around 15% maybe as much as 40% are still capable of insulin production. If the autoimmune process can be arrested even in this late stage, these cells can be preserved. The β cells have some limited capacity to replicate and precursors may form new β-cells.

Autoantigen Variants

Variants can differ from naturally occurring protein in amino acid sequence or in ways that do not involve sequence, or both. Non-sequence modifications include in vivo or in vitro chemical derivatization of the protein. Non-sequence modifications include changes in acetylation, methylation, phosphorylation, carboxylation, or glycosylation.

Preferred variants include an autoantigen, e.g., preproinsulin or an immunologically active fragment thereof (e.g., insulin B-chain, A chain, C peptide), GAD65, islet tyrosine phosphatase ICA512/IA-2, ICA12, ICA69, HSP60, carboxypeptidase H, peripherin, gangliosides (e.g., GM1-2, GM3) or immunologically active fragments thereof, whose sequences differ from the wild-type sequence by one or more conservative amino acid substitutions or by one or more non-conservative amino acid substitutions, deletions, or insertions which do not abolish the immunogenic activity. In a preferred embodiment, the sequence can differ from wild-type sequence by no more than 20% of the amino acid residues. In another preferred embodiment, the sequence can differ from wild-type sequence by 1, 2, 3, 5, 10, but not more than 20 to 30 amino acid residues. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S—Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S—Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase immunogenicity or peptide stability. Such analogs may contain, for example, one or more non-peptide bonds (which replace the peptide bonds) in the peptide sequence. Also included are analogs that include residues other than naturally occurring L-amino acids, e.g., D-amino acids or non-naturally occurring or synthetic amino acids, e.g., β or γ amino acids; and cyclic analogs.

Production of Fragments and Variants

Generation of Fragments

Fragments of a protein, e.g., fragments of an autoantigen described herein, can be produced in several ways, e.g., by chemical synthesis, recombinantly, or by proteolytic digestion. Chemical synthesis of immunologically active autoantigen fragments is preferred.

Fragments can be chemically synthesized using techniques known in the art such as conventional solid-phase peptide synthesis, e.g., Merrifield solid phase f-Moc or t-Boc chemistry. Synthetic peptides can be prepared under sterile conditions to a high level of purity, suitable for administration to humans. An autoantigen of the present invention may be arbitrarily divided into fragments of desired length with no overlap of the fragments, or divided into overlapping fragments of a desired length. These fragments can then be chemically synthesized and tested for immunogenic activity as described herein below. For example, overlapping or non-overlapping fragments (e.g., fragments of between 4-100 amino acid residues, preferably between 10-60 amino acid residues, more preferably between 20-50 amino acid residues) of the 110 amino acid sequence of preproinsulin (SEQ ID NO: 1) can easily be made by chemical synthesis and tested for immunogenic activity by a method described herein. Fragments of any of the type 1 diabetes autoantigens described herein can be similarly made and tested.

Internal or terminal fragments of an autoantigen described herein can also be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods, which are all known in the art.

Generation of Analogs: Production of Altered DNA and Peptide Sequences by Random Methods Amino acid sequence variants of a protein can be prepared by random mutagenesis of DNA which encodes a protein or a particular domain or region of a protein, e.g., an autoantigen described herein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, *Technique* 1:11-15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. AG Walton, Amsterdam: Elsevier pp 273-289; Itakura et al. (1984) *Annu. Rev. Biochem*. 53:323; Itakura et al. (1984) *Science* 198:1056; Ike et al. (1983) *Nucleic Acid Res*. 11:477.

Such techniques have been employed in the directed evolution of other proteins (see, for example, Scott et al. (1990) *Science* 249:386-390; Roberts et al. (1992) *PNAS* 89:2429-2433; Devlin et al. (1990) *Science* 249: 404-406; Cwirla et al. (1990) *PNAS* 87: 6378-6382; as well as U.S. Pat. Nos. 5,223, 409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1-3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081-1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* USA, 1978, 75: 5765).

Cassette Mutagenesis

Another method for preparing variants, cassette mutagenesis, is based on the technique described by Wells et al. (*Gene*, 1985 34:315). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Screens for Activity

The assays described above can be followed by secondary screens to identify immunologically active variants or fragments. For example, a standard animal screening assay can be developed in which the ability of a protein variant or fragment to generate an immune response, e.g., in a rodent, can be used to identify immunologically active fragments and variants from a group of candidates isolated though one of the primary screens described above.

Therefore, methods for generating fragments and variants and testing them for activity are known in the art. Once the core sequence of interest is identified, it is routine for one of ordinary skill in the art to obtain variants and fragments.

Fusion Proteins

An autoantigen or variant or fragment thereof can be fused to another protein or portion thereof. For example, an autoantigen can be operably linked to another polypeptide or other moiety to enhance its stability or immunogenicity. Examples of polypeptides that can be fused with an autoantigen described herein or portions thereof include, e.g., artificial T helper cell epitopes for immune stimulation of synthetic peptide immunogens (as described, e.g., in U.S. Pat. Nos. 6,228, 987 and 6,025,468) and other synthetic peptide carriers (See, e.g., U.S. Pat. No. 5,736,146) and low molecular weight immune stimulants (See U.S. Pat. No. 6,007,819).

EXAMPLES

Example 1

Preparation of Insulin B-Chain

Human insulin was made by standard solid-phase peptide synthesis (SPPS) procedure, described herein. The assembly strategy used in the protein synthesis was ABI (Applied Biosystem Inc.)-Fmoc/Thr. The Fmoc group protects the α-amino group of the amino acid. The peptide was assembled from the C-terminal towards the N-terminal with the α-carboxyl group of the starting amino acid attached to a solid support (resin). The resin used for assembly was polystyrene bead, an insoluble support with size of 400-1000 micron in diameter swelled after washing with NMP (N-methylpyrrolidone). The resin was preloaded with the first amino acid (Thr) from the C-terminal.

Chain Assembly

The first step in chain assembly is deprotection, or removal of the protecting group The Fmoc protecting group is removed by 22% piperidine. Conductimetric feedback of carbamate salt formed via removal of Fmoc group with piperidine/NMP showed the coupling efficacy.

After deprotection, the next amino acid is activated and coupled to the deprotected amino end of the growing peptide and forms the peptide bond. Activation of the incoming amino acid carboxyl group was achieved by HBTU/HOBt.

Between coupling, the column was washed with methanol and NMP (N-methylpyrrolidone), which swells the resin and washes out residues.

The cycle is repeated until a peptide of desired length is achieved.

A wash step is performed with DCM (dichloromethane), which removes NMP from the resin, followed by thorough washing with highly volatile methanol, an easily removable solvent which evaporates and dries.

Cleavage from the Resin and Removal of Side-Chain Protecting Groups.

A cleavage mixture was prepared (0.75 g crystalline phenol+0.25 g ethanedithiol+0.5 ml thioanisol+0.5 ml deionized H2O+10 ml trifluoroaceticacid). The dried peptide-resin was incubated in cool flask in ice bath (10 ml mixture/100-150 mg peptide-resin) for 1.5 h. Then the peptide was isolated from the reaction mixture by glass funnel filtration under high vacuum. The peptide was precipitated with cold methyl t-butyl ether (MTBE) and vacuum dried.

Purification Under Sterile Condition.

This step was performed with reverse phase HPLC. Buffer A=0.1% trifluoroaceticacid (TFA) and buffer B=70% acetonitrile, 30% H2O, 0.09% trifluoroaceticacid (TFA). By using a C18 column, the elution of the sample was based upon hydrophobicity (hydrophilic sample elutes earlier). The peak detection was performed by absorbance measurement of peptide bond at 214 nm and identified by mass spectrometry. The desired fraction was pooled in sterile vials and lyophilized with sample taken for AAA (amino acid analysis) analytical rpHPLC and Mass Spectrometry.

The results of quality control tests on the B-chain produced are shown below.

TABLE 2

Certificate of Analysis for SPPS B-chain-final product

| Parameter | Test to use | Range | Result |
|---|---|---|---|
| Appearance | Visual observation - solution | Clear | Clear |
| pH | pH meter | 3.5-4.5 | 4.0 |
| Strength | Protein concentration (Bio-Rad Assay Bio-Rad Laboratories) | 3.5-4.5 mg/ml | 3.82 mg/ml |
| Immuno-reactivity/potency | Human insulin RIA (Diagnostic System Laboratories Kit) | 10-30 uU/mg protein/ml | 80.2 uU/ml |
| Purity | HPLC | Area % >95% | >99% |
| Impurity | Total Residual Solvent (acetonitrile) gas chromatography | <500 ppm (particle per million) | <20 ppm (particle per million) |
| Identity | Mass Spectrometry | 3400-3450Da | Single major peak 3428.7Da |
| | Amino acid sequence Analyzer | 30 amino acid of human insulin B-chain sequence | 30 amino acid of human insulin B-chain sequence |
| Pyrogens | standard USP method | Meets requirement for absence of pyrogens | Meets requirement for absence of pyrogens |
| Sterility | | Sterile | Sterile |

Example 2

Solubilization of Insulin B-Chain

The insulin B chain is a hydrophobic molecule. Preferably, the synthesized insulin B chain is solubilized and maintained in soluble form for use in the vaccine.

The insulin B-chain can be treated to increase its solubility, e.g., to counter the effect of its hydrophobicity. This can be done by acidification and/or by using 4M urea buffer and/or by reducing cysteine with DTT to avoid dimerization.

Example 3

Method of Vaccine/Emulsion Preparation

The vaccine for human use was prepared under conditions suitable for human administration. The vaccine contains two components: an adjuvant, and insulin B-chain.

The first component is insulin B-chain, prepared and solubilized as described in Examples 1 and 2.

The second component is an IFA, e.g., Montanide ISA51 (Seppic Inc. France; Drug Master-file No: 10870DMF) or an equivalent composition. This IFA has been used in our animal studies and showed no systemic or significant local side effect.

The injections were prepared fresh, immediately before administration, as an emulsion, in a lamina-flow protected hood, under sterile conditions by using high pressure sterile syringes with an 18 gauge spatial connector. 2 mg of insulin B-chain (0.5 ml) was mixed with Montanide ISA51 (0.5 ml). An equivalent composition can be used. The emulsion is a 50/50 (weight by weight) emulsion. The emulsion was given intramuscularly to an adult human subject in a 1 ml volume in the thigh.

A number of embodiments of the invention have been described. Nevertheless, it will be understood that various modifications may be made without departing from the spirit and scope of the invention. Accordingly, other embodiments are within the scope of the following claims.

What is claimed is:

1. A pharmaceutical composition comprising an emulsion of an aqueous phase comprising human insulin B-chain consisting of amino acids 25-54 of SEQ ID NO:1 in about 3M-5M urea; and an oil phase comprising an oil-based adjuvant and an emulsifier or surfactant.

2. The pharmaceutical composition of claim 1, wherein the insulin B-chain is a synthetic peptide.

3. The pharmaceutical composition of claim 1, wherein the oil phase comprises Montanide ISA.

4. The pharmaceutical composition of claim 1, wherein the oil phase comprises Montanide 80.

5. The pharmaceutical composition of claim 1, wherein the pH of the composition is between 3.5-4.5.

6. The pharmaceutical composition of claim 1, wherein the oil phase comprises incomplete Freund's adjuvant (IFA).

7. The pharmaceutical composition of claim 1, wherein the oil phase comprises mannide oleate.

8. The pharmaceutical composition of claim 1, wherein the oil phase comprises mannide monooleate.

9. The pharmaceutical composition of claim 1, wherein the oil-based adjuvant is present at between 30-70% w/w.

10. The pharmaceutical composition of claim 1, which is a water-in-oil emulsion.

11. The pharmaceutical composition of claim 3, which is a water-in-oil emulsion.

12. The pharmaceutical composition of claim 1, wherein the emulsion is a 50-50% w/w emulsion of insulin B chain peptide and incomplete Freund's adjuvant (IFA).

* * * * *

SEQUENCE LISTING

<160> NUMBER OF SEQ ID NOS: 6

<210> SEQ ID NO 1
<211> LENGTH: 110
<212> TYPE: PRT
<213> ORGANISM: Homo sapiens

<400> SEQUENCE: 1

Met Ala Leu Trp Met Arg Leu Leu Pro Leu Leu Ala Leu Leu Ala Leu
 1               5                  10                  15

Trp Gly Pro Asp Pro Ala Ala Phe Val Asn Gln His Leu Cys Gly
                20                  25                  30

Ser His Leu Val Glu Ala Leu Tyr Leu Val Cys Gly Glu Arg Gly Phe
             35                  40                  45

Phe Tyr Thr Pro Lys Thr Arg Arg Glu Ala Glu Asp Leu Gln Val Gly
         50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 2
<211> LENGTH: 585
<212> TYPE: PRT
<213> ORGANISM: Homo sapiens

<400> SEQUENCE: 2

Met Ala Ser Pro Gly Ser Gly Phe Trp Ser Phe Gly Ser Glu Asp Gly
 1               5                  10                  15

Ser Gly Asp Ser Glu Asn Pro Gly Thr Ala Arg Ala Trp Cys Gln Val
                20                  25                  30

Ala Gln Lys Phe Thr Gly Gly Ile Gly Asn Lys Leu Cys Ala Leu Leu
             35                  40                  45

Tyr Gly Asp Ala Glu Lys Pro Ala Glu Ser Gly Gly Ser Gln Pro Pro
         50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
            115                 120                 125

Ser Thr Lys Val Ile Asp Phe His Tyr Pro Asn Glu Leu Leu Gln Glu
        130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
            195                 200                 205

```
Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
                260                 265                 270

Leu Ile Ala Phe Thr Ser Glu His Ser His Phe Ser Leu Lys Lys Gly
            275                 280                 285

Ala Ala Ala Leu Gly Ile Gly Thr Asp Ser Val Ile Leu Ile Lys Cys
            290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
                340                 345                 350

Ile Cys Lys Lys Tyr Lys Ile Trp Met His Val Asp Ala Ala Trp Gly
            355                 360                 365

Gly Gly Leu Leu Met Ser Arg Lys His Lys Trp Lys Leu Ser Gly Val
        370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
    450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
        515                 520                 525

Val Ala Pro Val Ile Lys Ala Arg Met Met Glu Tyr Gly Thr Thr Met
    530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585

<210> SEQ ID NO 3
<211> LENGTH: 979
<212> TYPE: PRT
<213> ORGANISM: Homo sapiens

<400> SEQUENCE: 3
```

-continued

```
Met Arg Arg Pro Arg Pro Gly Gly Leu Gly Ser Gly Gly Leu
 1               5                  10              15
Arg Leu Leu Leu Cys Leu Leu Leu Ser Ser Arg Pro Gly Gly Cys
             20                  25              30
Ser Ala Val Ser Ala His Gly Cys Leu Phe Asp Arg Arg Leu Cys Ser
             35                  40              45
His Leu Glu Val Cys Ile Gln Asp Gly Leu Phe Gly Gln Cys Gln Val
 50                  55                  60
Gly Val Gly Gln Ala Arg Pro Leu Leu Gln Val Thr Ser Pro Val Leu
 65              70                  75              80
Gln Arg Leu Gln Gly Val Leu Arg Gln Leu Met Ser Gln Gly Leu Ser
                 85                  90              95
Trp His Asp Asp Leu Thr Gln Tyr Val Ile Ser Gln Glu Met Glu Arg
                100                 105             110
Ile Pro Arg Leu Arg Pro Pro Glu Pro Arg Pro Arg Asp Arg Ser Gly
            115                 120             125
Leu Ala Pro Lys Arg Pro Gly Pro Ala Gly Glu Leu Leu Leu Gln Asp
         130                 135             140
Ile Pro Thr Gly Ser Ala Pro Ala Gln His Arg Leu Pro Gln Pro
145                 150             155                 160
Pro Val Gly Lys Gly Gly Ala Gly Ala Ser Ser Leu Ser Pro Leu
                165             170                 175
Gln Ala Glu Leu Leu Pro Pro Leu Leu Glu His Leu Leu Pro Pro
             180                 185             190
Gln Pro Pro His Pro Ser Leu Ser Tyr Glu Pro Ala Leu Leu Gln Pro
             195                 200             205
Tyr Leu Phe His Gln Phe Gly Ser Arg Asp Gly Ser Arg Val Ser Glu
210                 215                 220
Gly Ser Pro Gly Met Val Ser Val Gly Pro Leu Pro Lys Ala Glu Ala
225                 230                 235             240
Pro Ala Leu Phe Ser Arg Thr Ala Ser Lys Gly Ile Phe Gly Asp His
                245                 250                 255
Pro Gly His Ser Tyr Gly Asp Leu Pro Gly Pro Ser Ala Gln Leu
                260                 265             270
Phe Gln Asp Ser Gly Leu Leu Tyr Leu Ala Gln Glu Leu Pro Ala Pro
             275                 280             285
Ser Arg Ala Arg Val Pro Arg Leu Pro Glu Gln Gly Ser Ser Ser Arg
290                 295                 300
Ala Glu Asp Ser Pro Glu Gly Tyr Glu Lys Glu Gly Leu Gly Asp Arg
305                 310                 315                 320
Gly Glu Lys Pro Ala Ser Pro Ala Val Gln Pro Asp Ala Ala Leu Gln
                325                 330             335
Arg Leu Ala Ala Val Leu Ala Gly Tyr Gly Val Glu Leu Arg Gln Leu
             340                 345             350
Thr Pro Glu Gln Leu Ser Thr Leu Leu Thr Leu Leu Gln Leu Leu Pro
             355                 360             365
Lys Gly Ala Gly Arg Asn Pro Gly Gly Val Val Asn Val Gly Ala Asp
370                 375             380
Ile Lys Lys Thr Met Glu Gly Pro Val Glu Gly Arg Asp Thr Ala Glu
385                 390                 395             400
Leu Pro Ala Arg Thr Ser Pro Met Pro Gly His Pro Thr Ala Ser Pro
                405             410                 415
Thr Ser Ser Glu Val Gln Gln Val Pro Ser Pro Val Ser Glu Pro
             420                 425             430
```

```
Pro Lys Ala Ala Arg Pro Pro Val Thr Pro Val Leu Leu Glu Lys Lys
            435                 440                 445

Ser Pro Leu Gly Gln Ser Gln Pro Thr Val Ala Gly Gln Pro Ser Ala
    450                 455                 460

Arg Pro Ala Ala Glu Glu Tyr Gly Tyr Ile Val Thr Asp Gln Lys Pro
465                 470                 475                 480

Leu Ser Leu Ala Ala Gly Val Lys Leu Leu Glu Ile Leu Ala Glu His
                485                 490                 495

Val His Met Ser Ser Gly Ser Phe Ile Asn Ile Ser Val Val Gly Pro
            500                 505                 510

Ala Leu Thr Phe Arg Ile Arg His Asn Glu Gln Asn Leu Ser Leu Ala
            515                 520                 525

Asp Val Thr Gln Gln Ala Gly Leu Val Lys Ser Glu Leu Glu Ala Gln
            530                 535                 540

Thr Gly Leu Gln Ile Leu Gln Thr Gly Val Gly Gln Arg Glu Ala
545                 550                 555                 560

Ala Ala Val Leu Pro Gln Thr Ala His Ser Thr Ser Pro Met Arg Ser
                565                 570                 575

Val Leu Leu Thr Leu Val Ala Leu Ala Gly Val Ala Gly Leu Leu Val
            580                 585                 590

Ala Leu Ala Val Ala Leu Cys Val Arg Gln His Ala Arg Gln Gln Asp
            595                 600                 605

Lys Glu Arg Leu Ala Ala Leu Gly Pro Glu Gly Ala His Gly Asp Thr
            610                 615                 620

Thr Phe Glu Tyr Gln Asp Leu Cys Arg Gln His Met Ala Thr Lys Ser
625                 630                 635                 640

Leu Phe Asn Arg Ala Glu Gly Pro Pro Glu Pro Ser Arg Val Ser Ser
                645                 650                 655

Val Ser Ser Gln Phe Ser Asp Ala Ala Gln Ala Ser Pro Ser Ser His
                660                 665                 670

Ser Ser Thr Pro Ser Trp Cys Glu Glu Pro Ala Gln Ala Asn Met Asp
            675                 680                 685

Ile Ser Thr Gly His Met Ile Leu Ala Tyr Met Glu Asp His Leu Arg
            690                 695                 700

Asn Arg Asp Arg Leu Ala Lys Glu Trp Gln Ala Leu Cys Ala Tyr Gln
705                 710                 715                 720

Ala Glu Pro Asn Thr Cys Ala Thr Ala Gln Gly Glu Gly Asn Ile Lys
                725                 730                 735

Lys Asn Arg His Pro Asp Phe Leu Pro Tyr Asp His Ala Arg Ile Lys
            740                 745                 750

Leu Lys Val Glu Ser Ser Pro Ser Arg Ser Asp Tyr Ile Asn Ala Ser
            755                 760                 765

Pro Ile Ile Glu His Asp Pro Arg Met Pro Ala Tyr Ile Ala Thr Gln
            770                 775                 780

Gly Pro Leu Ser His Thr Ile Ala Asp Phe Trp Gln Met Val Trp Glu
785                 790                 795                 800

Ser Gly Cys Thr Val Ile Val Met Leu Thr Pro Leu Val Glu Asp Gly
                805                 810                 815

Val Lys Gln Cys Asp Arg Tyr Trp Pro Asp Glu Gly Ala Ser Leu Tyr
            820                 825                 830

His Val Tyr Glu Val Asn Leu Val Ser Glu His Ile Trp Cys Glu Asp
            835                 840                 845

Phe Leu Val Arg Ser Phe Tyr Leu Lys Asn Val Gln Thr Gln Glu Thr
```

```
                           850                 855                 860
Arg Thr Leu Thr Gln Phe His Phe Leu Ser Trp Pro Ala Glu Gly Thr
865                 870                 875                 880

Pro Ala Ser Thr Arg Pro Leu Leu Asp Phe Arg Lys Val Asn Lys
                885                 890                 895

Cys Tyr Arg Gly Arg Ser Cys Pro Ile Ile Val His Cys Ser Asp Gly
                900                 905                 910

Ala Gly Arg Thr Gly Thr Tyr Ile Leu Ile Asp Met Val Leu Asn Arg
                915                 920                 925

Met Ala Lys Gly Val Lys Glu Ile Asp Ile Ala Ala Thr Leu Glu His
            930                 935                 940

Val Arg Asp Gln Arg Pro Gly Leu Val Arg Ser Lys Asp Gln Phe Glu
945                 950                 955                 960

Phe Ala Leu Thr Ala Val Ala Glu Glu Val Asn Ala Ile Leu Lys Ala
                965                 970                 975

Leu Pro Gln

<210> SEQ ID NO 4
<211> LENGTH: 622
<212> TYPE: PRT
<213> ORGANISM: Homo sapiens

<400> SEQUENCE: 4

Met Ser Met Arg Ser Pro Ile Ser Ala Gln Leu Ala Leu Asp Gly Val
1               5                   10                  15

Gly Thr Met Val Asn Cys Thr Ile Lys Ser Glu Glu Lys Lys Glu Pro
            20                  25                  30

Cys His Glu Ala Pro Gln Gly Ser Ala Thr Ala Ala Glu Pro Gln Pro
        35                  40                  45

Gly Asp Pro Ala Arg Ala Ser Gln Asp Ser Ala Asp Pro Gln Ala Pro
    50                  55                  60

Ala Gln Gly Asn Phe Arg Gly Ser Trp Asp Cys Ser Ser Pro Glu Gly
65                  70                  75                  80

Asn Gly Ser Pro Glu Pro Lys Arg Pro Gly Ala Ser Glu Ala Ala Ser
                85                  90                  95

Gly Ser Gln Glu Lys Leu Asp Phe Asn Arg Asn Leu Lys Glu Val Val
            100                 105                 110

Pro Ala Ile Glu Lys Leu Leu Ser Ser Asp Trp Lys Glu Arg Phe Leu
        115                 120                 125

Gly Arg Asn Ser Met Glu Ala Lys Asp Val Lys Gly Thr Gln Glu Ser
    130                 135                 140

Leu Ala Glu Lys Glu Leu Gln Leu Leu Val Met Ile His Gln Leu Ser
145                 150                 155                 160

Thr Leu Arg Asp Gln Leu Leu Thr Ala His Ser Glu Gln Lys Asn Met
                165                 170                 175

Ala Ala Met Leu Phe Glu Lys Gln Gln Gln Met Glu Leu Ala Arg
            180                 185                 190

Gln Gln Gln Glu Gln Ile Ala Lys Gln Gln Gln Leu Ile Gln Gln
        195                 200                 205

Gln His Lys Ile Asn Leu Leu Gln Gln Gln Ile Gln Gln Val Asn Met
    210                 215                 220

Pro Tyr Val Met Ile Pro Ala Phe Pro Pro Ser His Gln Pro Leu Pro
225                 230                 235                 240

Val Thr Pro Asp Ser Gln Leu Ala Leu Pro Ile Gln Pro Ile Pro Cys
                245                 250                 255
```

```
Lys Pro Val Glu Tyr Pro Leu Gln Leu Leu His Ser Pro Pro Ala Pro
              260                 265                 270

Val Val Lys Arg Pro Gly Ala Met Ala Thr His His Pro Leu Gln Glu
              275                 280                 285

Pro Ser Gln Pro Leu Asn Leu Thr Ala Lys Pro Lys Ala Pro Glu Leu
          290                 295                 300

Pro Asn Thr Ser Ser Pro Ser Leu Lys Met Ser Ser Cys Val Pro
305                 310                 315                 320

Arg Pro Pro Ser His Gly Gly Pro Thr Arg Asp Leu Gln Ser Ser Pro
              325                 330                 335

Pro Ser Leu Pro Leu Gly Phe Leu Gly Glu Gly Asp Ala Val Thr Lys
              340                 345                 350

Ala Ile Gln Asp Ala Arg Gln Leu Leu His Ser His Ser Gly Ala Leu
              355                 360                 365

Asp Gly Ser Pro Asn Thr Pro Phe Arg Lys Asp Leu Ile Ser Leu Asp
      370                 375                 380

Ser Ser Pro Ala Lys Glu Arg Leu Glu Asp Gly Cys Val His Pro Leu
385                 390                 395                 400

Glu Glu Ala Met Leu Ser Cys Asp Met Asp Gly Ser Arg His Phe Pro
              405                 410                 415

Glu Ser Arg Asn Ser Ser His Ile Lys Arg Pro Met Asn Ala Phe Met
              420                 425                 430

Val Trp Ala Lys Asp Glu Arg Arg Lys Ile Leu Gln Ala Phe Pro Asp
              435                 440                 445

Met His Asn Ser Ser Ile Ser Lys Ile Leu Gly Ser Arg Trp Lys Ser
      450                 455                 460

Met Thr Asn Gln Glu Lys Gln Pro Tyr Tyr Glu Glu Gln Ala Arg Leu
465                 470                 475                 480

Ser Arg Gln His Leu Glu Lys Tyr Pro Asp Tyr Lys Tyr Lys Pro Arg
              485                 490                 495

Pro Lys Arg Thr Cys Ile Val Glu Gly Lys Arg Leu Arg Val Gly Glu
              500                 505                 510

Tyr Lys Ala Leu Met Arg Thr Arg Arg Gln Asp Ala Arg Gln Ser Tyr
              515                 520                 525

Val Ile Pro Pro Gln Ala Gly Gln Val Gln Met Ser Ser Ser Asp Val
              530                 535                 540

Leu Tyr Pro Arg Ala Ala Gly Met Pro Leu Ala Gln Pro Leu Val Glu
545                 550                 555                 560

His Tyr Val Pro Arg Ser Leu Asp Pro Asn Met Pro Val Ile Val Asn
              565                 570                 575

Thr Cys Ser Leu Arg Glu Glu Gly Glu Gly Thr Asp Asp Arg His Ser
              580                 585                 590

Val Ala Asp Gly Glu Met Tyr Arg Tyr Ser Glu Asp Glu Asp Ser Glu
              595                 600                 605

Gly Glu Glu Lys Ser Asp Gly Glu Leu Val Val Leu Thr Asp
              610                 615                 620

<210> SEQ ID NO 5
<211> LENGTH: 483
<212> TYPE: PRT
<213> ORGANISM: Homo sapiens

<400> SEQUENCE: 5

Met Ser Gly His Lys Cys Ser Tyr Pro Trp Asp Leu Gln Asp Arg Tyr
1               5                   10                  15
```

```
Ala Gln Asp Lys Ser Val Val Asn Lys Met Gln Gln Arg Tyr Trp Glu
             20                  25                  30
Thr Lys Gln Ala Phe Ile Lys Ala Thr Gly Lys Lys Glu Asp Glu His
         35                  40                  45
Val Val Ala Ser Asp Ala Asp Leu Asp Ala Lys Leu Glu Leu Phe His
 50                  55                  60
Ser Ile Gln Arg Thr Cys Leu Asp Leu Ser Lys Ala Ile Val Leu Tyr
 65                  70                  75                  80
Gln Lys Arg Ile Cys Phe Leu Ser Gln Glu Glu Asn Glu Leu Gly Lys
                 85                  90                  95
Phe Leu Arg Ser Gln Gly Phe Gln Asp Lys Thr Arg Ala Gly Lys Met
             100                 105                 110
Met Gln Ala Thr Gly Lys Ala Leu Cys Phe Ser Ser Gln Arg Leu
         115                 120                 125
Ala Leu Arg Asn Pro Leu Cys Arg Phe His Gln Glu Val Glu Thr Phe
 130                 135                 140
Arg His Arg Ala Ile Ser Asp Thr Trp Leu Thr Val Asn Arg Met Glu
 145                 150                 155                 160
Gln Cys Arg Thr Glu Tyr Arg Gly Ala Leu Leu Trp Met Lys Asp Val
                 165                 170                 175
Ser Gln Glu Leu Asp Pro Asp Leu Tyr Lys Gln Met Gly Lys Phe Arg
             180                 185                 190
Lys Val Gln Thr Gln Val Arg Leu Ala Lys Lys Asn Phe Asp Lys Leu
             195                 200                 205
Lys Met Asp Val Cys Gln Lys Val Asp Leu Leu Gly Ala Ser Arg Cys
 210                 215                 220
Asn Leu Leu Ser His Met Leu Ala Thr Tyr Gln Thr Thr Leu Leu His
 225                 230                 235                 240
Phe Trp Glu Lys Thr Ser His Thr Met Ala Ala Ile His Glu Ser Phe
                 245                 250                 255
Lys Gly Tyr Gln Pro Tyr Glu Phe Thr Thr Leu Lys Ser Leu Gln Asp
             260                 265                 270
Pro Met Lys Lys Leu Val Glu Lys Glu Lys Lys Ile Asn Gln
             275                 280                 285
Gln Glu Ser Thr Asp Ala Ala Val Gln Glu Pro Ser Gln Leu Ile Ser
 290                 295                 300
Leu Glu Glu Glu Asn Gln Arg Lys Glu Ser Ser Phe Lys Thr Glu
 305                 310                 315                 320
Asp Gly Lys Ser Ile Leu Ser Ala Leu Asp Lys Gly Ser Thr His Thr
                 325                 330                 335
Ala Cys Ser Gly Pro Ile Asp Glu Leu Leu Asp Met Lys Ser Glu Glu
             340                 345                 350
Gly Ala Cys Leu Gly Pro Val Ala Gly Thr Pro Glu Pro Glu Gly Ala
             355                 360                 365
Asp Lys Asp Asp Leu Leu Leu Ser Glu Ile Phe Asn Ala Ser Ser
 370                 375                 380
Leu Glu Glu Gly Glu Phe Ser Lys Glu Trp Ala Ala Val Phe Gly Asp
 385                 390                 395                 400
Gly Gln Val Lys Glu Pro Val Pro Thr Met Ala Leu Gly Glu Pro Asp
                 405                 410                 415
Pro Lys Ala Gln Thr Gly Ser Gly Phe Leu Pro Ser Gln Leu Leu Asp
             420                 425                 430
Gln Asn Met Lys Asp Leu Gln Ala Ser Leu Gln Glu Pro Ala Lys Ala
```

```
                        435                 440                 445
Ala Ser Asp Leu Thr Ala Trp Phe Ser Leu Phe Ala Asp Leu Asp Pro
            450                 455                 460

Leu Ser Asn Pro Asp Ala Val Gly Lys Thr Asp Lys Glu His Glu Leu
465                 470                 475                 480

Leu Asn Ala

<210> SEQ ID NO 6
<211> LENGTH: 471
<212> TYPE: PRT
<213> ORGANISM: Homo sapiens

<400> SEQUENCE: 6

Met Ser His His Pro Ser Gly Leu Arg Ala Gly Phe Ser Thr Ser
  1               5                  10                  15

Tyr Arg Arg Thr Phe Gly Pro Pro Ser Leu Ser Pro Gly Ala Phe
                 20                  25                  30

Ser Tyr Ser Ser Ser Ser Arg Phe Ser Ser Ser Arg Leu Leu Gly Ser
                 35                  40                  45

Ala Ser Pro Ser Ser Ser Val Arg Leu Gly Ser Phe Arg Ser Pro Arg
 50                  55                  60

Ala Gly Ala Gly Ala Leu Leu Arg Leu Pro Ser Glu Arg Leu Asp Phe
 65                  70                  75                  80

Ser Met Ala Glu Ala Leu Asn Gln Glu Phe Leu Ala Thr Arg Ser Asn
                 85                  90                  95

Glu Lys Gln Glu Leu Gln Glu Leu Asn Asp Arg Phe Ala Asn Phe Ile
                100                 105                 110

Glu Lys Val Arg Phe Leu Glu Gln Gln Asn Ala Ala Leu Arg Gly Glu
                115                 120                 125

Leu Ser Gln Ala Arg Gly Gln Glu Pro Ala Arg Ala Asp Gln Leu Cys
                130                 135                 140

Gln Gln Glu Leu Arg Glu Leu Arg Arg Glu Leu Glu Leu Leu Gly Arg
145                 150                 155                 160

Glu Arg Asp Arg Val Gln Val Glu Arg Asp Gly Leu Ala Glu Asp Leu
                165                 170                 175

Ala Ala Leu Lys Gln Arg Leu Glu Glu Glu Thr Arg Lys Arg Glu Asp
                180                 185                 190

Ala Glu His Asn Leu Val Leu Phe Arg Lys Asp Val Asp Asp Ala Thr
                195                 200                 205

Leu Ser Arg Leu Glu Leu Glu Arg Lys Ile Glu Ser Leu Met Asp Glu
                210                 215                 220

Ile Glu Phe Leu Lys Lys Leu His Glu Glu Glu Leu Arg Asp Leu Gln
225                 230                 235                 240

Val Ser Val Glu Ser Gln Gln Val Gln Gln Val Glu Val Glu Ala Thr
                245                 250                 255

Val Lys Pro Glu Leu Thr Ala Ala Leu Arg Asp Ile Arg Ala Gln Tyr
                260                 265                 270

Glu Ser Ile Ala Ala Lys Asn Leu Gln Glu Ala Glu Glu Trp Tyr Lys
                275                 280                 285

Ser Lys Tyr Ala Asp Leu Ser Asp Ala Ala Asn Arg Asn His Glu Ala
                290                 295                 300

Leu Arg Gln Ala Lys Gln Glu Met Asn Glu Ser Arg Arg Gln Ile Gln
305                 310                 315                 320

Ser Leu Thr Cys Glu Val Asp Gly Leu Arg Gly Thr Asn Glu Ala Leu
                325                 330                 335
```

-continued

```
Leu Arg Gln Leu Arg Glu Leu Glu Glu Gln Phe Ala Leu Glu Ala Gly
            340                 345                 350

Gly Tyr Gln Ala Gly Ala Ala Arg Leu Glu Glu Glu Leu Arg Gln Leu
        355                 360                 365

Lys Glu Glu Met Ala Arg His Leu Arg Glu Tyr Gln Glu Leu Leu Asn
    370                 375                 380

Val Lys Met Ala Leu Asp Ile Glu Ile Ala Thr Tyr Arg Lys Leu Leu
385                 390                 395                 400

Glu Gly Glu Glu Ser Arg Ile Ser Val Pro Val His Ser Phe Ala Ser
                405                 410                 415

Leu Asn Ile Lys Thr Thr Val Pro Glu Val Glu Pro Pro Gln Asp Ser
            420                 425                 430

His Ser Arg Lys Thr Val Leu Ile Lys Thr Ile Glu Thr Arg Asn Gly
        435                 440                 445

Glu Gln Val Val Thr Glu Ser Gln Lys Glu Gln Arg Ser Glu Leu Asp
    450                 455                 460

Lys Ser Ser Ala His Ser Tyr
465                 470
```